US011065028B2

(12) United States Patent
Farhangnia et al.

(10) Patent No.: US 11,065,028 B2
(45) Date of Patent: *Jul. 20, 2021

(54) METHOD AND APPARATUS FOR PLACING A CATHETER WITHIN A VASCULATURE

(71) Applicant: ROXWOOD MEDICAL INC., Redwood City, CA (US)

(72) Inventors: Mehrdad Farhangnia, San Francisco, CA (US); John Miller, Redwood City, CA (US); Mark Taber, St. Louis, MO (US); Mark C. Yang, San Francisco, CA (US)

(73) Assignee: ROXWOOD MEDICAL INC., Redwood City, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 16/164,647

(22) Filed: Oct. 18, 2018

(65) Prior Publication Data

US 2019/0117250 A1 Apr. 25, 2019

Related U.S. Application Data

(60) Continuation of application No. 14/813,173, filed on Jul. 30, 2015, now Pat. No. 10,130,385, which is a (Continued)

(51) Int. Cl.
*A61B 17/3207* (2006.01)
*A61M 25/04* (2006.01)
(Continued)

(52) U.S. Cl.
CPC ......... *A61B 17/3207* (2013.01); *A61M 25/04* (2013.01); *A61B 2017/22042* (2013.01);
(Continued)

(58) Field of Classification Search
CPC .. A61B 17/320725; A61B 2017/22042; A61B 2017/22044; A61B 2017/22069;
(Continued)

(56) References Cited

U.S. PATENT DOCUMENTS 4,854,325 A 8/1989 Stevens
4,894,051 A 1/1990 Shiber
(Continued)

FOREIGN PATENT DOCUMENTS

EP 0189329 A2 7/1986
EP 0418677 A1 3/1991
(Continued)

OTHER PUBLICATIONS

EP Application No. 08772056: European Search Report dated Mar. 19, 2012.
(Continued)

*Primary Examiner* — Patrick Fernandes
(74) *Attorney, Agent, or Firm* — Seager, Tufte & Wickhem, LLP

(57) ABSTRACT

A catheter for insertion into vasculature of a patient to a target area in the vasculature includes a hollow inner shaft, a non-occluding self-expandable scaffold coupled to the distal end of the inner shaft and disposed at the distal end of the inner shaft, and a hollow outer shaft. The outer shaft is slidable over the inner shaft and scaffold such that the scaffold is in a non-expanded state when the outer shaft is around the scaffold. The outer shaft has a state where the distal end of the outer shaft remains near the target area without the inner shaft and the scaffold being within the outer shaft. The inner shaft and the scaffold are removable through the proximal end of the outer shaft while the distal end of the outer shaft remains near the target area.

15 Claims, 25 Drawing Sheets

Related U.S. Application Data continuation of application No. 14/223,458, filed on Mar. 24, 2014, now Pat. No. 9,125,683, which is a continuation-in-part of application No. 14/060,381, filed on Oct. 22, 2013, now Pat. No. 9,358,037, which is a continuation-in-part of application No. 13/842,744, filed on Mar. 15, 2013, now Pat. No. 9,126,020, which is a continuation-in-part of application No. 13/166,623, filed on Jun. 22, 2011, now Pat. No. 8,764,730, which is a division of application No. 12/147,130, filed on Jun. 26, 2008, now Pat. No. 7,988,646, said application No. 14/223,458 is a continuation-in-part of application No. 13/842,744, filed on Mar. 15, 2013, now Pat. No. 9,126,020, and a continuation-in-part of application No. 13/166,623, filed on Jun. 22, 2011, now Pat. No. 8,764,730.

(60) Provisional application No. 61/793,268, filed on Mar. 15, 2013, provisional application No. 61/716,856, filed on Oct. 22, 2012, provisional application No. 61/064,715, filed on Mar. 21, 2008, provisional application No. 60/996,057, filed on Oct. 26, 2007, provisional application No. 60/960,900, filed on Oct. 19, 2007, provisional application No. 60/929,395, filed on Jun. 26, 2007.

(51) Int. Cl.
  *A61M 25/10* (2013.01)
  *A61M 25/00* (2006.01)
  *A61B 17/22* (2006.01)
  *A61M 25/09* (2006.01)

(52) U.S. Cl.
  CPC ............. *A61B 2017/22044* (2013.01); *A61B 2017/22069* (2013.01); *A61B 2017/22094* (2013.01); *A61M 25/104* (2013.01); *A61M 2025/0042* (2013.01); *A61M 2025/09175* (2013.01); *A61M 2025/09183* (2013.01)

(58) Field of Classification Search
  CPC .... A61B 2017/22094; A61M 25/0068; A61M 25/0074; A61M 25/008; A61M 25/04; A61M 2025/0046; A61M 2025/0681; A61M 2025/0042; A61M 2025/0293; A61M 25/104; A61M 2025/09175; A61M 2025/09183
  See application file for complete search history.

(56) References Cited

U.S. PATENT DOCUMENTS

| | | |
|---|---|---|
| 4,898,575 A | 2/1990 | Fischell et al. |
| 4,917,094 A | 4/1990 | Lynch et al. |
| 4,983,165 A | 1/1991 | Loiterman |
| 5,002,560 A | 3/1991 | Machold et al. |
| 5,071,407 A | 12/1991 | Termin et al. |
| 5,221,261 A | 6/1993 | Termin et al. |
| 5,334,166 A | 8/1994 | Palestrant |
| 5,378,239 A | 1/1995 | Termin et al. |
| 5,456,667 A | 10/1995 | Ham et al. |
| 5,480,423 A | 1/1996 | Ravenscroft et al. |
| 5,484,407 A | 1/1996 | Osypka |
| 5,496,277 A | 3/1996 | Termin et al. |
| 5,509,900 A | 4/1996 | Kirkman |
| 5,514,073 A | 5/1996 | Miyata et al. |
| 5,575,771 A | 11/1996 | Walinsky |
| 5,628,761 A | 5/1997 | Rizik |
| 5,769,821 A | 6/1998 | Abrahamson et al. |
| 5,824,055 A | 10/1998 | Spriridigliozzi et al. |
| 5,824,058 A | 10/1998 | Ravenscroft et al. |
| 5,908,405 A | 6/1999 | Imran et al. |
| 5,947,924 A | 9/1999 | Liprie |
| 6,059,812 A | 5/2000 | Clerc et al. |
| 6,071,227 A | 6/2000 | Popowski et al. |
| 6,071,263 A | 6/2000 | Kirkman |
| 6,071,285 A | 6/2000 | Lashinski et al. |
| 6,126,649 A | 10/2000 | VanTassel et al. |
| 6,159,139 A | 12/2000 | Chiu |
| 6,165,209 A | 12/2000 | Patterson et al. |
| 6,210,408 B1 | 4/2001 | Chandrasekaran et al. |
| 6,221,006 B1 | 4/2001 | Dubrul et al. |
| 6,234,952 B1 | 5/2001 | Liprie |
| 6,251,132 B1 | 6/2001 | Ravenscroft et al. |
| 6,371,978 B1 | 4/2002 | Wilson |
| 6,398,708 B1 | 6/2002 | Hastings et al. |
| 6,416,523 B1 | 7/2002 | Lafontaine |
| 6,425,898 B1 | 7/2002 | Wilson et al. |
| 6,454,775 B1 | 9/2002 | Demarais et al. |
| 6,544,253 B1 | 4/2003 | Tanner |
| 6,558,349 B1 | 5/2003 | Kirkman |
| 6,562,031 B2 | 5/2003 | Chandrasekaran et al. |
| 6,579,302 B2 | 6/2003 | Duerig et al. |
| 6,596,005 B1 | 7/2003 | Kanz et al. |
| 6,660,014 B2 | 12/2003 | Demarais et al. |
| 6,695,858 B1 | 2/2004 | Dubrul et al. |
| 6,702,830 B1 | 3/2004 | Demarais et al. |
| 6,808,531 B2 | 10/2004 | Lafontaine et al. |
| 6,835,203 B1 | 12/2004 | Vardi et al. |
| 6,855,136 B2 | 2/2005 | Dorros et al. |
| 6,932,829 B2 | 8/2005 | Majercak |
| 6,945,977 B2 | 9/2005 | Demarais et al. |
| 6,989,071 B2 | 1/2006 | Kocur et al. |
| 7,037,320 B2 | 5/2006 | Brady et al. |
| 7,131,981 B2 | 11/2006 | Appling et al. |
| 7,144,364 B2 | 12/2006 | Barbut et al. |
| 7,169,160 B1 | 1/2007 | Middleman et al. |
| 7,306,617 B2 | 12/2007 | Majercak |
| 7,396,358 B2 | 7/2008 | Appling et al. |
| 7,485,139 B1 | 2/2009 | Ciamacco, Jr. |
| 7,655,016 B2 | 2/2010 | Demarais et al. |
| 7,691,081 B2 | 4/2010 | Crossman |
| 7,758,626 B2 | 7/2010 | Kim et al. |
| 7,771,401 B2 | 8/2010 | Hekmat et al. |
| 7,842,056 B2 | 11/2010 | Holman et al. |
| 7,846,175 B2 | 12/2010 | Bonnette et al. |
| 7,922,687 B2 | 4/2011 | Gingles |
| 7,927,363 B2 | 4/2011 | Perouse |
| 7,988,646 B2 | 8/2011 | Taber |
| 8,062,258 B2 | 11/2011 | Demarais et al. |
| 8,066,757 B2 | 11/2011 | Ferrera et al. |
| 8,070,761 B2 | 12/2011 | Weber et al. |
| 8,075,519 B2 | 12/2011 | Min et al. |
| 8,100,935 B2 | 1/2012 | Rosenbluth et al. |
| 8,118,827 B2 | 2/2012 | Duerig et al. |
| 8,152,951 B2 | 4/2012 | Zawacki et al. |
| 8,162,964 B2 | 4/2012 | Piippo et al. |
| 8,556,926 B2 | 10/2013 | Duerig et al. |
| 8,608,688 B2 | 12/2013 | Jain |
| 8,728,106 B2 | 5/2014 | Weber et al. |
| 8,764,730 B2 | 7/2014 | Taber |
| 8,777,977 B2 | 7/2014 | Angel |
| 8,961,555 B2 | 2/2015 | Duerig et al. |
| 8,968,350 B2 | 3/2015 | Duerig et al. |
| 9,125,683 B2 | 9/2015 | Farhangnia et al. |
| 9,126,016 B2 | 9/2015 | Fulton |
| 9,126,020 B2 | 9/2015 | Farhangnia et al. |
| 9,358,037 B2 | 6/2016 | Farhangnia et al. |
| 9,364,255 B2 | 6/2016 | Weber |
| 9,408,626 B2 | 8/2016 | Tekulve |
| 10,039,896 B2 | 8/2018 | Kornowski et al. |
| 10,130,385 B2 | 11/2018 | Farhangnia et al. |
| 10,426,510 B2 | 10/2019 | Farhangnia et al. |
| 2002/0010487 A1 | 1/2002 | Evans et al. |
| 2002/0116147 A1 | 8/2002 | Vock et al. |
| 2002/0128677 A1 | 9/2002 | Duerig et al. |
| 2003/0055445 A1 | 3/2003 | Evans et al. |
| 2003/0078605 A1 | 4/2003 | Bashiri et al. |
| 2003/0097094 A1 | 5/2003 | Ouriel et al. |
| 2003/0163082 A1 | 8/2003 | Mertens |

(56) References Cited

U.S. PATENT DOCUMENTS

| | | |
|---|---|---|
| 2003/0171765 A1 | 9/2003 | Kokate et al. |
| 2003/0191434 A1 | 10/2003 | Dorros et al. |
| 2003/0236533 A1 | 12/2003 | Wilson et al. |
| 2003/0236564 A1 | 12/2003 | Majercak |
| 2004/0204738 A1 | 10/2004 | Weber et al. |
| 2004/0215220 A1 | 10/2004 | Dolan et al. |
| 2004/0220473 A1 | 11/2004 | Lualdi |
| 2005/0020974 A1 | 1/2005 | Noriega et al. |
| 2005/0085846 A1 | 4/2005 | Carrison et al. |
| 2005/0216044 A1 | 9/2005 | Hong |
| 2006/0069323 A1 | 3/2006 | Elkins et al. |
| 2006/0069421 A1 | 3/2006 | Murray, III |
| 2006/0079740 A1 | 4/2006 | Silver et al. |
| 2006/0149129 A1 | 7/2006 | Watts et al. |
| 2006/0155363 A1 | 7/2006 | LaDuca et al. |
| 2006/0155366 A1 | 7/2006 | LaDuca et al. |
| 2006/0189845 A1 | 8/2006 | Maahs et al. |
| 2006/0190070 A1 | 8/2006 | Dieck et al. |
| 2007/0010763 A1 | 1/2007 | Lentz et al. |
| 2007/0083215 A1 | 4/2007 | Hamer et al. |
| 2007/0123925 A1 | 5/2007 | Benjamin et al. |
| 2007/0135826 A1 | 6/2007 | Zaver et al. |
| 2007/0233220 A1 | 10/2007 | Greenan |
| 2007/0250035 A1 | 10/2007 | El-Nounou et al. |
| 2008/0027529 A1 | 1/2008 | Hartley et al. |
| 2008/0058839 A1 | 3/2008 | Nobles et al. |
| 2009/0005757 A1 | 1/2009 | Taber |
| 2009/0048577 A1 | 2/2009 | Gillies et al. |
| 2009/0048654 A1 | 2/2009 | Chmura et al. |
| 2009/0062840 A1 | 3/2009 | Angel |
| 2009/0105642 A1 | 4/2009 | Leonard et al. |
| 2009/0105644 A1 | 4/2009 | Leonard et al. |
| 2009/0105737 A1 | 4/2009 | Fulkerson et al. |
| 2009/0292307 A1 | 11/2009 | Razack |
| 2010/0114113 A1 | 5/2010 | Dubrul et al. |
| 2010/0204712 A1 | 8/2010 | Mallaby |
| 2010/0280450 A1 | 11/2010 | Jain |
| 2010/0286465 A1 | 11/2010 | Benson |
| 2010/0292614 A1 | 11/2010 | Delaney |
| 2010/0331951 A1 | 12/2010 | Bei et al. |
| 2011/0022038 A1 | 1/2011 | Seshadri et al. |
| 2011/0137163 A1 | 6/2011 | Eder |
| 2011/0160763 A1 | 6/2011 | Ferrera et al. |
| 2011/0251591 A1 | 10/2011 | Taber |
| 2011/0288578 A1 | 11/2011 | Angel |
| 2011/0295234 A1 | 12/2011 | Eaton |
| 2012/0022579 A1 | 1/2012 | Fulton |
| 2012/0046730 A1 | 2/2012 | von Oepen et al. |
| 2012/0101561 A1 | 4/2012 | Porter |
| 2012/0197277 A1 | 8/2012 | Stinis |
| 2012/0239064 A1 | 9/2012 | Cartier et al. |
| 2012/0259314 A1 | 10/2012 | Guo et al. |
| 2012/0316600 A1 | 12/2012 | Ferrera et al. |
| 2013/0253347 A1 | 9/2013 | Griswold et al. |
| 2013/0253474 A1 | 9/2013 | Farhangnia et al. |
| 2013/0317534 A1 | 11/2013 | Zhou et al. |
| 2014/0052103 A1 | 2/2014 | Cully et al. |
| 2014/0128844 A1 | 5/2014 | Kornowski et al. |
| 2014/0207179 A1 | 7/2014 | Farhangnia et al. |
| 2014/0249511 A1 | 9/2014 | Taber |
| 2014/0257352 A1 | 9/2014 | Weber et al. |
| 2014/0277008 A1 | 9/2014 | Farhangnia et al. |
| 2014/0277015 A1 | 9/2014 | Stinis |
| 2014/0288583 A1 | 9/2014 | Stinis |
| 2015/0073538 A1 | 3/2015 | Thomas et al. |
| 2015/0126967 A1 | 5/2015 | Taber |
| 2015/0157215 A1 | 6/2015 | Stigall |
| 2015/0157216 A1 | 6/2015 | Stigall et al. |
| 2015/0250991 A1 | 9/2015 | Silvestro |
| 2015/0297250 A1 | 10/2015 | Farhat et al. |
| 2015/0313479 A1 | 11/2015 | Stigall et al. |
| 2015/0328433 A1 | 11/2015 | Farhangnia et al. |
| 2015/0335345 A1 | 11/2015 | Farhangnia et al. |
| 2015/0343178 A1 | 12/2015 | Fulton, III |
| 2016/0022293 A1 | 1/2016 | Dubrul et al. |
| 2016/0066936 A1 | 3/2016 | Weber et al. |
| 2016/0235429 A1 | 8/2016 | Farhangnia et al. |

FOREIGN PATENT DOCUMENTS

| | | |
|---|---|---|
| EP | 0592726 A1 | 4/1994 |
| EP | 0592726 B1 | 3/1997 |
| EP | 829271 A2 | 3/1998 |
| EP | 1025813 A2 | 8/2000 |
| EP | 1225949 A1 | 7/2002 |
| EP | 1237488 A1 | 9/2002 |
| EP | 1365830 A1 | 12/2003 |
| EP | 1496972 A2 | 1/2005 |
| EP | 1534181 A2 | 6/2005 |
| EP | 1610718 A2 | 1/2006 |
| EP | 1637084 A1 | 3/2006 |
| EP | 1642539 A1 | 4/2006 |
| EP | 1699518 A1 | 9/2008 |
| EP | 1970083 A1 | 9/2008 |
| EP | 1970093 A1 | 9/2008 |
| EP | 2203209 A1 | 7/2010 |
| EP | 2262567 A1 | 12/2010 |
| EP | 2670318 A1 | 12/2013 |
| EP | 2714172 A1 | 4/2014 |
| EP | 2908783 A1 | 8/2015 |
| EP | 2977072 A1 | 1/2016 |
| EP | 3043747 A1 | 7/2016 |
| EP | 3043748 A1 | 7/2016 |
| GB | 2472213 A | 2/2011 |
| JP | 11076419 A | 3/1999 |
| JP | 2002537943 A | 11/2002 |
| JP | 2004525691 A | 8/2004 |
| JP | 2010531715 A | 9/2010 |
| JP | 2011502655 A | 1/2011 |
| JP | 2015517392 A | 6/2015 |
| WO | 9510317 A1 | 4/1995 |
| WO | 0053120 A1 | 9/2000 |
| WO | 02067772 A2 | 9/2002 |
| WO | 02070061 A1 | 9/2002 |
| WO | 2004026180 A2 | 4/2004 |
| WO | 2007062879 A1 | 6/2007 |
| WO | 2008051898 A2 | 5/2008 |
| WO | 2009003113 A1 | 12/2008 |
| WO | 2009114046 A2 | 9/2009 |
| WO | 2010102307 A1 | 9/2010 |
| WO | 2011119879 A1 | 9/2011 |
| WO | 2012160562 A1 | 11/2012 |
| WO | 2012160562 A9 | 2/2013 |
| WO | 2013177383 A1 | 11/2013 |
| WO | 2014066412 A1 | 5/2014 |
| WO | 2014066412 A9 | 9/2014 |

OTHER PUBLICATIONS

Extended European Search Report dated Dec. 4, 2015 in related European Application 15181301.1.

PCT/US08/68380: International Search Report dated Oct. 2, 2008.

PCT/US13/66217: International Preliminary Report on Patentability dated Sep. 16, 2014.

PCT/US13/66217: International Search Report and Written Opinion dated Jan. 16, 2014.

PCT/US2015/021975: International Search Report and Written Opinion dated Jun. 26, 2015.

EP Application No. 08772056: European Search Report dated Mar. 29, 2012.

PCT/US15/021975: International Search Report and Written Opinion dated Jun. 26, 2015.

Extended European Search Report dated May 3, 2016 in related European Application No. 13848899.4.

Office Action in corresponding Japanese Application No. 2017-502761, dated Nov. 27, 2018, along with an English language translation (8 pages).

Non-Final Office Action issued in U.S. Appl. No. 14/596,950, dated Jan. 10, 2019, 14 pages.

Notification of Reasons for Refusal issued in counterpart Japanese Patent Application No. 2017-200224 dated Feb. 12, 2019.

(56) References Cited

OTHER PUBLICATIONS

Notification of Reasons for Refusal issued in related Japanese Patent Application No. 2017-502761 dated Jul. 9, 2019.
Extended European search Report dated Oct. 23, 2017 in related European Application No. 15770295.2, 8 pages.

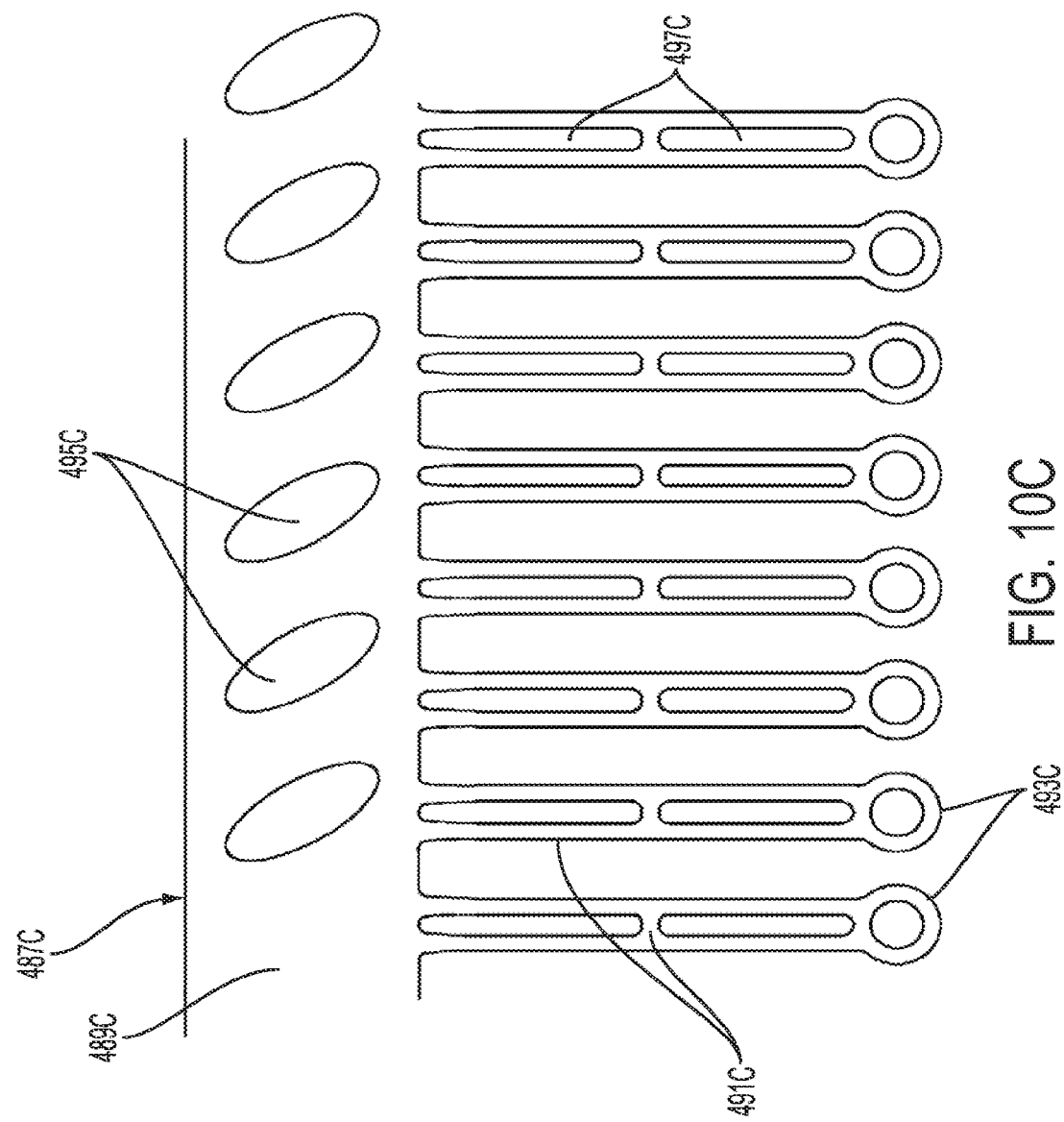

METHOD AND APPARATUS FOR PLACING A CATHETER WITHIN A VASCULATURE

CROSS-REFERENCE TO RELATED APPLICATIONS

This application is a continuation of U.S. application Ser. No. 14/813,173 filed on Jul. 30, 2015, which is a continuation application of U.S. patent application Ser. No. 14/223,458, filed Mar. 24, 2014, which is a continuation-in-part of: (1) U.S. patent application Ser. No. 14/060,381 filed Oct. 22, 2013; (2) U.S. application Ser. No. 13/842,744, filed Mar. 15, 2013; and (3) U.S. application Ser. No. 13/166,623, filed Jun. 22, 2011, the contents of each of which are incorporated by reference in their entireties.

U.S. patent application Ser. No. 14/060,381 is a continuation-in-part of U.S. application Ser. No. 13/842,744, and claims priority to U.S. Provisional Application No. 61/793,268, filed Mar. 15, 2013, and U.S. Provisional Application No. 61/716,856, filed Oct. 22, 2012, the contents of each of which are incorporated by reference in their entireties.

U.S. application Ser. No. 13/842,744 is a continuation-in-part application of U.S. application Ser. No. 13/166,623, and claims priority to U.S. Provisional Application No. 61/716,856 the contents of each of which are incorporated by reference in their entireties.

U.S. application Ser. No. 13/166,623, which issued as U.S. Pat. No. 8,764,730 on Jul. 1, 2014, is a divisional application of U.S. application Ser. No. 12/147,130, filed Jun. 26, 2008, which issued as U.S. Pat. No. 7,988,646 on Aug. 2, 2011, which claims priority to U.S. Provisional Application No. 60/929,395, filed Jun. 26, 2007, U.S. Provisional Application No. 60/960,900, filed Oct. 19, 2007, U.S. Provisional Application No. 60/996,057, filed Oct. 26, 2007, and U.S. Provisional Application No. 61/064,715, filed Mar. 21, 2008, the contents of each of which are incorporated by reference in their entireties.

FIELD OF THE INVENTION

The invention relates generally to an apparatus and methods for treating vasculatures, and, more particularly, to methods and apparatus for crossing a chronic total occlusion of a vasculature and/or providing support and centering to facilitate a guidewire to cross through a chronic total occlusion.

BACKGROUND

A chronic total occlusion in a coronary artery, peripheral artery, vein, dialysis fistula, or other types of vasculature represents a challenge for percutaneous treatment. Percutaneous treatments are generally preferred revascularization options as compared to bypass surgery. Continuing improvements in equipment specifically developed for chronic total occlusions have allowed success rates to improve. Although the success rates for these types of procedures have improved, the procedures for percutaneous treatments still suffer from several drawbacks.

Patients without a successful percutaneous treatment may need to undergo bypass surgery or experience continuing symptoms from the occlusions.

A major obstacle within a chronic total occlusion may often be encountered while attempting to advance a catheter across the chronic total occlusion in a vasculature. A maximum resistance may be met at the most proximal point of the lesion, i.e. the firm, fibrous cap. While being advanced, a catheter may tend to deflect away from the fibrous cap towards the adventitial layer, often entering a false lumen. This off-axis displacement of the catheter often may result in a procedural failure.

Successful passage of the catheter may also be obstructed by randomly located calcified regions of atherosclerotic plaque within the mass of the lesion. Microchannels within the obstruction may be desirable targets for the tip of the catheter. However, these soft spots within the lesion are difficult to identify angiographically and are dispersed randomly within the matrix of the lesion.

Coronary arteries and other vasculatures tend to be non-linear conduits, often coursing over the surface of the epicardium and other tissues. The success of current technology is limited by this type of geometry. In current systems, a catheter or currently available catheter is advanced down a vasculature to the level of the obstruction. The catheter advancement may tend to proceed along the outer, greater curvature of the vasculature.

As a result, only a minor portion of the surface area of the obstruction may be encountered with sufficient force to allow passage of the catheter. On many occasions, the angle of encounter and/or the force applied to the fibrous cap may not be sufficient for crossing the fibrous cap with the catheter. If the tip of the catheter is curved prior to placement through the support catheter, direct longitudinal force may be compromised as the wire is advanced off axis. If a rapid exchange catheter system is used as catheter support, the catheter may buckle within the guide-catheter resulting in suboptimal longitudinal catheter force.

At times, a single lumen angioplasty balloon may be inflated just proximal to the chronic total occlusion in an attempt to center the catheter in the vessel lumen and provide additional support for the catheter. The angioplasty balloon, however, is occlusive to nearby vessels and exerts a significant outward force on the native vessel.

Approximately one-third of patients with coronary artery disease (CAD) and half of patients with peripheral artery disease (PAD), present with a chronic total occlusion (CTO) in the vessel. Despite overwhelming evidence of improved outcomes, attempted interventions remain low due to the lack of effective and convenient interventional tools. CTOs are characterized by fibrous caps with small micro-channels often in tortuous anatomy, leading to challenges for clinicians to gain guidewire access to treat the underlying disease.

In some situations, following an initial advancement of a first catheter to or through the cap of the occlusion, additional instruments or catheters may be subsequently advanced proximal to or through the occlusion. This may require removal of the first catheter and placement of a second catheter proximal to the occlusion. In placing the second catheter, the anatomy of the patient must be again be navigated, including the tortuous inner lumens of the heart, for example. However, the usual risks of the catheter being diverted off-course remain. Additionally, even if a guide wire is used, passage of the catheter through this anatomy can be traumatic for vessel walls.

Generally, needs exist for improved apparatus and methods for treating vasculatures.

More specifically, needs exist for improved apparatus and methods for efficiently and effectively passing a guidewire through a chronic total occlusion in a vasculature. In particular, there exists a need for improved apparatus and methods for efficiently and effectively passing a guidewire through a chronic total occlusion in a vasculature in such a way that the guidewire is reliably centered in the chronic total occlusion. Furthermore, there exists a need for improved apparatus and methods for navigating the vasculature in a way that is simple, reliable, and less traumatic to the vasculature.

SUMMARY OF THE INVENTION

One embodiment of the invention is a catheter apparatus for insertion into vasculature of a patient and to a target area in the vasculature. The catheter apparatus may include a hollow inner shaft with a distal end and a proximal end; a non-occluding self-expandable scaffold coupled to the distal end of the inner shaft and disposed at the distal end of the inner shaft, a portion of the distal end of the inner shaft being disposed at least in part inside the self-expandable scaffold; and a hollow outer shaft with a distal end and a proximal end. The outer shaft may be slidable over the inner shaft and the scaffold such that the scaffold is in a non-expanded state when the outer shaft is disposed around the scaffold. The outer shaft can have a state where the distal end of the outer shaft remains near the target area without the inner shaft and the scaffold being within the outer shaft. The inner shaft and the scaffold can be removable through the proximal end of the outer shaft while the proximal end of the outer shaft remains near the target area.

One embodiment of the invention is a method of using a catheter in a vessel of a patient for crossing a target area and providing support for a medical device. The catheter includes a hollow shaft with a distal end and a proximal end, and a non-occluding self-expandable scaffold disposed at the distal end of the catheter. A portion of the distal end of the catheter is disposed at least in part inside the scaffold. The catheter also includes a sheath with a central lumen, a distal end having a distal opening, and a proximal end having a proximal opening. The sheath is slidable along the shaft, and the scaffold may be coupled to the distal end of the catheter. The scaffold can be in an un-expanded state when covered by the sheath. The method may include withdrawing the sheath to expand the self-expandable scaffold. The method may also include inserting a catheter into a vessel; moving the sheath and the scaffold structure relative to each other to position the sheath at least partially over the scaffold structure so that the scaffold returns to the un-expanded state; and withdrawing the hollow shaft and the scaffold out through the proximal opening of the sheath. The sheath may remain in the vessel as a support catheter such that a medical device may be passed through the proximal opening of the sheath and advanced through the sheath to a target area near the distal end of the sheath.

Additional features, advantages, and embodiments of the invention are set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The foregoing summary, as well as the following detailed description of the invention, will be better understood when read in conjunction with the appended drawings. The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 10C is an unwrapped view of the alternate embodiment of a scaffold of the type shown in FIGS. 10A and 10B, but having an alternate configuration in accordance with principles of the invention.

DETAILED DESCRIPTION

Figure 1A:
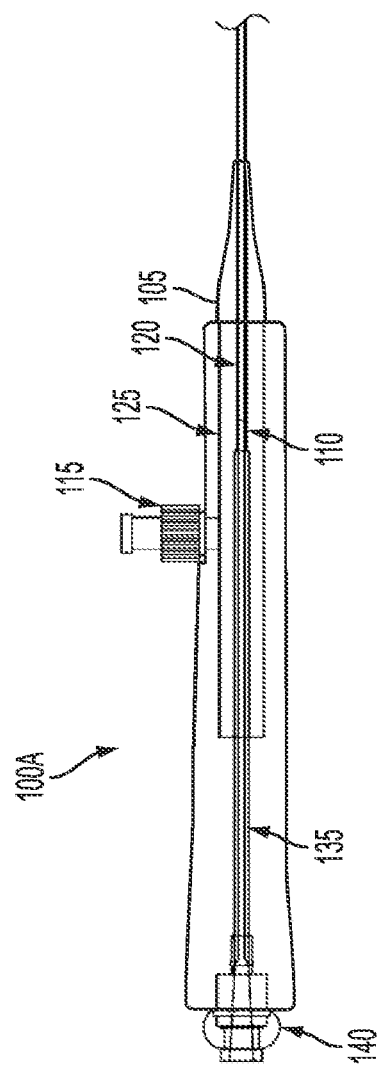
FIG. 1A is a view of the proximal end of a catheter apparatus in accordance with principles of the invention.

Embodiments of the present invention solve many of the problems and/or overcome many of the drawbacks and disadvantages of the prior art by providing an apparatus and method for treating vasculatures.

Embodiments of the present invention may include an apparatus and methods for advancing one or more catheters, preferably, microcatheters through chronic total occlusions in the vasculature. The support and centering functionality has application beyond CTOs, even though the preferred embodiments described herein are directed to support and centering to facilitate a guidewire to cross through a CTO.

In particular, embodiments of the invention may accomplish this with an apparatus for efficiently and effectively passing a microcatheter through the center of a chronic total occlusion in a vasculature. In particular, embodiments of the invention provide for apparatus and methods for centering a microcatheter within a vasculature, and for simplifying the insertion of multiple devices or microcatheters into the vasculature.

One embodiment of the invention is a catheter apparatus including: a microcatheter having a lumen, a distal opening and a distal end; one or more guidewires for passing through the lumen of the microcatheter; an inner shaft having a lumen, a distal opening and a distal end for allowing the microcatheter to pass through this inner shaft; an outer shaft having a lumen, a distal opening and a distal end for passing the outer shaft over the inner shaft; and a substantially cylindrical self-expandable scaffold structure having a distal end and a proximal end disposed towards the distal end of the inner shaft, wherein the proximal end of the structure is attached to the inner shaft, wherein the distal end is slidable along the shaft, and wherein the scaffold structure is configured so that the inner shaft runs through the center of the scaffold and wherein the scaffold structure is configured to be non-occluding. The microcatheter and inner shaft may be capable of being independently operable. The self-expandable scaffold may include loops, which project inwardly from the cylindrical plane of the scaffold. In one embodiment, the loops position the inner shaft approximately in the center of the cylindrical plane of the scaffold.

The self-expandable scaffold structure may be made from a variety of materials including nitinol. In one embodiment, the self-expandable scaffold includes a loop network at the distal end of the scaffold.

The apparatus may also include a sleeve disposed on the distal end of the self-expandable scaffold. The sleeve may hold the self-expandable scaffold in place without attaching the scaffold to the inner shaft such that the inner shaft and scaffold are separated by a gap.

In one embodiment, the outer shaft and inner shaft are flexible. In another embodiment, the distal end of the outer shaft is hydrophilic. This property may be achieved by means of a coating. Thus, in one embodiment, the distal end of the outer shaft includes a hydrophilic coating.

The lumen of the inner shaft and/or outer shaft may be configured to accommodate one or more guidewires. Thus, in one embodiment, the device includes one or more guidewires, which pass through the microcatheter. The microcatheter may be removable and/or highly flexible.

In one embodiment, the distal end of the outer shaft is beveled and tapered. This structure at the distal end of the outer shaft may aid with the proper positioning of the device in the vasculature.

The lumen of the inner shaft and/or outer shaft may be configured to accommodate one or more guidewires. Thus, in one embodiment, the device includes one or more guidewires in addition to the one or more guidewires, which pass through the microcatheter. In one embodiment, the distal end of the microcatheter is tapered. The microcatheter may be removable and/or highly flexible. The catheter apparatus may also include a handle body.

Another embodiment of the invention is a catheter apparatus including: a microcatheter having a lumen, a distal opening and a distal end; an inner shaft having a lumen, a distal opening and a distal end for passing the inner shaft over the microcatheter; an outer shaft having a lumen, a distal opening and a distal end for passing the outer shaft over the inner shaft; and a substantially cylindrical self-expandable scaffold structure having a proximal end and a distal end, disposed towards the distal end of the inner shaft wherein the proximal end of the structure is attached to the inner shaft, wherein the distal end is slidable along the shaft, and wherein the scaffold structure is configured so that the inner shaft runs through the center of the scaffold and wherein the scaffold structure is configured to be non-occluding. Optionally, the catheter apparatus includes one or more guidewires for passing through the lumen of the microcatheter and/or a handle body. The microcatheter is capable of being independently operable.

The self-expandable scaffold may include one or more loops, which project inwardly from the cylindrical plane of the scaffold. In one embodiment, the loops position the inner shaft approximately in the center of the cylindrical plane of the scaffold. The self-expandable scaffold may be made from nitinol. Optionally, the self-expandable scaffold includes a loop network at the distal end of the scaffold. A sleeve may also be disposed on the distal end of the self-expandable scaffold. The sleeve holds the self-expandable scaffold in position without attaching it to the shaft. The distal end of the scaffold may be separated from the shaft by a gap.

In one embodiment, the outer shaft and inner shaft are flexible. In another embodiment, the distal end of the outer shaft is hydrophilic. In yet another embodiment, the distal end of the outer shaft includes a hydrophilic coating.

The lumen of the inner shaft and/or outer shaft may be configured to accommodate one or more guidewires. In one embodiment, the distal end of the outer shaft is beveled and tapered. In another embodiment, the distal end of the microcatheter is tapered. The microcatheter may be removable and/or highly flexible.

Yet another embodiment of the invention is a catheter apparatus including: a microcatheter having a lumen, a distal opening and a distal end; an inner shaft having a lumen, a distal opening and a distal end for allowing the microcatheter to pass through this inner shaft; an outer shaft having a lumen, a distal opening and a distal end for passing the outer shaft over the inner shaft; and one or more self-expandable scaffold structures disposed towards the distal end of the inner shaft, wherein each of the one or more self-expandable scaffold structures includes a center band surrounding the inner shaft and one or more expansible arms attached to the center band. One of the one or more self-expandable scaffold structures may be on the distal end of the inner shaft. This scaffold may be configured to be non-occluding. The center band and/or arms of the scaffold may include one or more openings. Furthermore, the arms may curve. Preferably, microcatheter is capable of being independently operable. The apparatus may be configured to include a sleeve disposed on the distal end of the self-expandable scaffold (such as, e.g., over the center band). Alternatively, the ring may be glued to the scaffold. The outer shaft and inner shaft may be flexible. The distal end of the outer shaft may be hydrophilic via, e.g., use of a hydrophilic coating. The lumen of the inner shaft and/or outer shaft may be configured to accommodate one or more guidewires. The distal end of the outer shaft may be beveled and tapered. The distal end of the microcatheters may also be tapered. The microcatheter may be removable and/or highly flexible. The catheter apparatus may also include one or more guidewires for passing through the lumen of the microcatheter and/or a handle body.

Another embodiment of the invention is a method of operating such a catheter. In one embodiment, the method includes providing a catheter apparatus of the invention; inserting a guide catheter into a vasculature with a chronic total occlusion; inserting the catheter apparatus of into the guide catheter; advancing the catheter apparatus into contact with the chronic total occlusion; translating the outer shaft over self-expandable scaffold; allowing the self-expandable scaffold to expand; wherein the inner shaft is approximately centered on the inside of the self-expandable scaffold; and advancing the microcatheter apparatus into contact with the chronic total occlusion. In one embodiment, the inner shaft is approximately centered relative to the vasculature.

Another embodiment of the invention is a catheter apparatus including: a microcatheter having a lumen, a distal opening and a distal end; an inner shaft having a lumen, a distal opening and a distal end for passing the inner shaft over the microcatheter; an outer shaft having a lumen, a distal opening and a distal end for passing the outer shaft over the inner shaft; and a substantially cylindrical self-expandable scaffold structure having a proximal end and a distal end, disposed towards the distal end of the inner shaft, wherein the proximal end of the structure is attached to the inner shaft, wherein the distal end is slidable along the shaft, and wherein the scaffold structure is configured so that the inner shaft runs through the center of the scaffold and wherein the scaffold structure is configured to be non-occluding. The catheter apparatus may further include one or more guidewires for passing through the lumen of the microcatheter. The inner shaft and microcatheter may be capable of being independently operable. In one embodiment, the self-expandable scaffold includes loops, which project inwardly from the cylindrical plane of the scaffold. The loops may position the inner shaft approximately in the center of the cylindrical plane of the scaffold. The self-expandable scaffold may be made of nitinol. The self-expandable scaffold may also include a loop network at the distal end of the scaffold. Optionally, the apparatus may further include a sleeve disposed on the distal end of the self-expandable scaffold. The inner and outer shaft may be flexible. In one embodiment, distal end of the outer shaft is hydrophilic. In another embodiment, the distal end of the outer shaft includes a hydrophilic coating. The lumen of the inner shaft and/or outer shaft are configured to accommodate one or more guidewires. The distal end of the outer shaft may be beveled and tapered. For example, the distal end of the microcatheter may be tapered. The microcatheter may highly flexible and/or removable. The apparatus may also include a handle body.

Yet another embodiment of the invention is a catheter apparatus including a shaft having a lumen and one or more self-expandable scaffold structure disposed on the distal end of the end shaft, wherein the scaffold when expanded centers the lumen of the shaft. The apparatus may include one or more self-expandable scaffold structure. In certain embodiment, the self-expandable scaffold structure is substantially cylindrical, has a distal end and a proximal end and the proximal end is disposed towards the distal end of the inner shaft. In certain embodiments, the self-expandable scaffold structure includes loops, which project inwardly from the cylindrical plane of the scaffold. The inward facing loops may be attached to the scaffold. The shaft may pass through the loops. In one embodiment, the self-expandable scaffold structure is substantially cylindrical, has a distal end and a proximal end, wherein the distal end is crimped and the proximal end is disposed towards the distal end of the inner shaft. In another embodiment, the self-expandable scaffold structure is substantially cylindrical, has a distal tip and a proximal end, wherein the distal tip is configured for passing the shaft and wherein the proximal end is disposed towards the distal end of the inner shaft. In certain embodiments, the self-expandable scaffold does not include loops, which project inwardly from the cylindrical plane of the scaffold. In one embodiment, each of the one or more self-expandable scaffold structures includes a center band surrounding the inner shaft and one or more expansible arms attached to the center band.

Another embodiment of the invention is a method of centering a microcatheter in vessel including: inserting a microcatheter having one or more self-expandable scaffold structure towards the distal end of the microcatheter in a vessel, wherein the self-expandable scaffold structure is covered by an outer shaft, and withdrawing the outer shaft to expand the self-expandable scaffold structure whereby expansion of the scaffold centers the microcatheter. In certain embodiments, the microcatheter includes one self-expandable scaffold structure. The self-expandable scaffold structure may be substantially cylindrical, has a distal end and a proximal end and wherein the proximal end is disposed towards the distal end of the microcatheter. In another embodiment, the self-expandable scaffold structure includes loops, which project inwardly from the cylindrical plane of the scaffold. The inward facing loops may be attached to the scaffold. The shaft may pass through the loop. In certain embodiments, expansion of the scaffold centers the microcatheter inside scaffold thereby approximately centering the microcatheter in the vessel. In one embodiment, the self-expandable scaffold structure is substantially cylindrical, has a distal end and a proximal end, wherein the distal end is crimped and wherein the proximal end is disposed towards the distal end of the inner shaft. In another embodiment, the self-expandable scaffold structure is substantially cylindrical, has a distal tip and a proximal end, wherein the distal tip is configured for passing the shaft and wherein the proximal end is disposed towards the distal end of the inner shaft. In certain embodiments, the self-expandable scaffold does not include loops which project inwardly from the cylindrical plane of the scaffold. In certain embodiments, expansion of the scaffold may center the microcatheter inside scaffold thereby approximately centering the microcatheter in the vessel. In another embodiment, each of the one or more self-expandable scaffold structures includes a center band surrounding the inner shaft and one or more expansible arms attached to the center band.

Another embodiment of the invention is a catheter apparatus including: a hollow shaft with a distal end and a proximal end, and a non-occluding self-expandable scaffold having a central longitudinal axis, the self-expandable scaffold being disposed at the distal end of the catheter, wherein a portion of the distal end of the catheter is disposed at least in part inside the self-expandable scaffold, wherein the distal end is slidable along the shaft, and wherein the scaffold is configured to be coupled to the distal end of the catheter, wherein at least a portion of the distal end of the catheter is disposed substantially along the central axis of the self-expandable scaffold structure. The catheter apparatus may further include a sheath for sliding over the hollow shaft. The catheter apparatus may also further include a microcatheter having a lumen, a distal opening, and a distal end. In one embodiment, inner shaft and microcatheter are capable of being independently operable. In another embodiment, the microcatheter includes comprising one or more guidewires for passing through the lumen of the microcatheter. The microcatheter may be more rigid and less flexible than the one or more guidewires. The self-expandable scaffold includes loops which project inwardly from the cylindrical plane of the scaffold to the central longitudinal axis of the self-expandable scaffold structure. In certain embodiments, the loops position the shaft approximately along the central longitudinal axis of the self-expandable scaffold structure. The self-expandable scaffold may be made of nitinol. The self-expandable scaffold may also include a loop network at the distal end of the scaffold. The sheath and shaft may be flexible. The distal end of the shaft may be hydrophilic. Alternatively, the distal end of the sheath includes a hydrophilic coating. In one embodiment, the distal end of the microcatheter is tapered. In another embodiment, the microcatheter is removable or highly flexible. The catheter apparatus may also include a handle body.

Yet another embodiment of the invention is a method of centering a microcatheter in vessel comprising: inserting a microcatheter into vessel, wherein the microcatheter includes a hollow shaft with a distal end and a proximal end, a non-occluding self-expandable scaffold having a central longitudinal axis, the self-expandable scaffold being disposed at the distal end of the catheter, wherein a portion of the distal end of the catheter is disposed at least in part inside the self-expandable scaffold, and a sheath wherein the distal end is slidable along the shaft, wherein the scaffold is configured to be coupled to the distal end of the catheter, wherein at least a portion of the distal end of the catheter is disposed substantially along the central axis of the self-expandable scaffold structure, wherein the hollow shaft is covered by the sheath; and withdrawing the sheath to expand the self-expandable scaffold structure whereby expansion of the scaffold centers the microcatheter along the central longitudinal axis of the scaffold thereby centering the microcatheter in the vessel. In certain embodiments, the microcatheter may be a microcatheter as described above. In one embodiment, the method also includes inserting a guidewire through the microcatheter. In one embodiment, the vessel has a chronic occlusion and the method further includes advancing the microcatheter in contact with the chronic occlusion. In certain embodiments, the self-expandable scaffold includes loops, which project inwardly from the cylindrical plane of the scaffold to the central longitudinal axis of the self-expandable scaffold structure. The loops may position the shaft approximately along the central longitudinal axis of the self-expandable scaffold structure.

Another embodiment is a method of treating a chronic total occlusion with a catheter apparatus of the invention. In one embodiment, the inner shaft is approximately centered relative to the vasculature.

Embodiments of the present invention may incorporate several features to successfully center a microcatheter in a chronic occlusion. Features of the present invention may include a catheter apparatus comprising an outer shaft having a lumen, an inner shaft having a lumen, a microcatheter having a lumen, one or more guidewires for passing through the lumen of the microcatheter and a scaffold structure whereby the scaffold structure is attached to the inner shaft, and whereby the inner shaft and microcatheter telescope independently of each other. The scaffold is configured to be non-occluding, allowing blood to flow through. Features of the present invention also include expansion or activation of a distal tip for creating a scaffold structure.

The apparatus of the invention are able to mitigate deflection of the guidewire tip in a vessel during treatment of a chronic total occlusion. In particular, the distal end of the microcatheter serves to protect and provide support, such as stable or rigid support, for the one or more guidewires. In certain embodiments, the microcatheter may act an independent guidewire support.

The devices of the invention offers a simple and stable platform from which clinicians can effectively treat these challenging chronic total occlusion lesions with a guidewire of their choice. Using nitinol scaffolding and a centering core lumen, the catheter may provide interventionalists a stable entry point into the true lumen. In certain embodiments, self-expanding scaffolding (e.g. made of nitinol) provides for anchoring at the lesion. In particular, the anchoring may be atraumatic and non-occlusive. Devices of the invention provide for a reliable centering access of the guidewire. Moreover, the configuration of devices of the invention allow for co-axial alignment such that the lumen of the device (and therefore the guidewire) is centrally aligned with the CTO cap.

In certain embodiments of the invention, the devices of the invention provide for non-occlusive anchoring (via the self-expandable scaffold). The devices of the invention also provide for complete support of the guidewire. Due to the configuration, the operation of the device is simple and repeatable. Thus, the devices of the invention may be used in an antegrade approach.

Figure 1B:
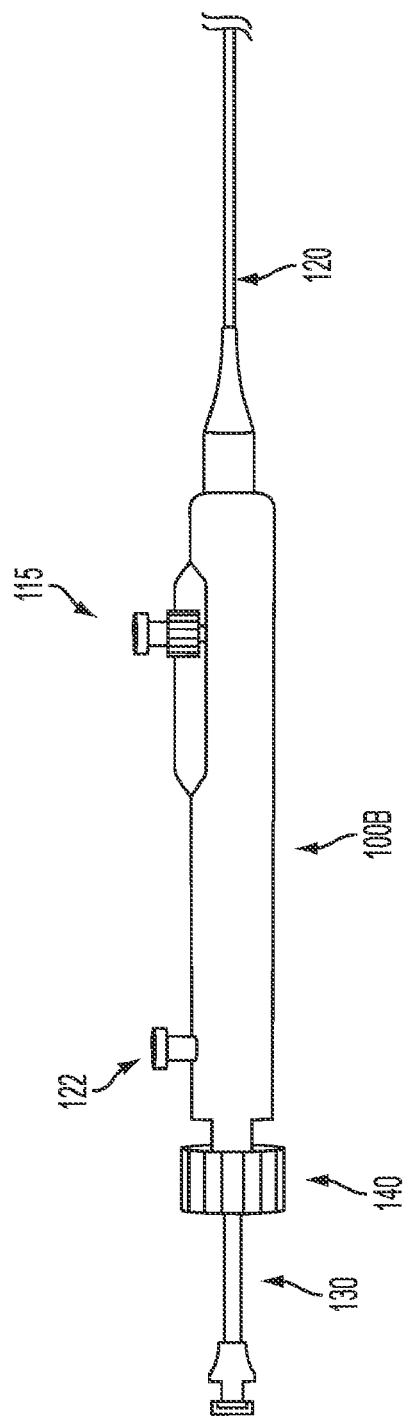
FIG. 1B is another view of the proximal end of a catheter apparatus in accordance with principles of the invention.

FIGS. 1A and 1B show exemplary embodiments of a proximal end of a catheter system in accordance with the principles of the invention. The distal end of the system is not shown in these figures and can embody the various embodiments described and shown in the figures and description described herein and subsequently.

FIG. 1A shows a partial break-away view of a proximal end of a catheter apparatus according to one embodiment of the invention. The proximal end includes a handle body 100A. Handle body 100A of the catheter apparatus includes a lumen through which outer shaft 110 can pass. The outer shaft may be attached the handle. The outer shaft also includes a lumen though which inner shaft 120 may pass.

Inner shaft 120 has a lumen through which one or more microcatheter (not shown) may pass and inner shaft 120 extends distally to be associated with a scaffold (not shown); both the microcatheter and the scaffold are discussed in more detail in the following description and figures. Toward the proximal end of handle body 100A is hemostasis valve 140. Towards the distal end of the handle 100 is thumb lever 115. The thumb lever 115 may be adjustable. In one embodiment, thumb lever 115 is may be adjustable to hold outer shaft 110 in place.

Tip 105 may be located at the distal end of handle body 100A. In one embodiment, the tip 105 provides for a step-wise taper. Alternatively, the tip 105 provides gradual taper. In one embodiment, the taper serves to provide strain relief on the handle. In one embodiment, the tip end is integral with the outer shaft assembly 125. In another embodiment of the invention, the tip is integral with the handle body 100A.

Outer shaft assembly 125 is located toward the distal end of handle body 100A. Outer shaft assembly 125 extends from the proximal end of handle body 100A into the interior. Outer shaft assembly 125 may be integral with handle body 100A. Thumb lever 115 may be connected to the outer shaft assembly 125.

The outer shaft 110 and/or inner shaft 120 may be surrounded by an internal reinforcement shaft 135. The internal reinforcement shaft 135 may extend from approximately the proximal end to approximately distal end of the handle body 100A. In one embodiment, the reinforcement shaft extends the entire length of the handle body 100A. In another embodiment, the reinforcement shaft 135 only extends to the outer shaft assembly 125. In an alternate embodiment, the reinforcement shaft 135 extends into or through the outer shaft assembly 125. Reinforcement shaft 135 may be integral with the handle body 100A. Reinforcement shaft 135 may be a rigid tube that surrounds the outer shaft 110 and/or inner shaft 120. In one embodiment, the proximal end of the outer shaft is located at proximal end of the outer shaft assembly 125. The internal reinforcement shaft 135 is adjacent to or connected to the proximal end of outer shaft assembly 125. The inner shaft 120 passes through the internal reinforcement shaft 135 and then through the outer shaft 110. The internal reinforcement shaft 135 may be configured so that it prevents buckling of the inner shaft 120. Furthermore, the length and configuration of the internal reinforcement shaft 135 may vary depending on the contemplated use. The internal reinforcement shaft 135 may span all or part of the entire length of the handle body 100A.

FIG. 1B shows another view of a handle of a catheter apparatus according to one embodiment of the invention. Handle body 100B of the catheter apparatus includes a lumen through which outer shaft 110 (not shown) can pass. The outer shaft may be attached the handle. The outer shaft also includes a lumen though which inner shaft 120 may pass. Inner shaft 120 has a lumen through which one or more microcatheters (for example, FIG. 4, microcatheter 130) may pass. Each of the one or more microcatheters has a lumen through which one or more guidewires may pass. The handle further includes hemostasis valve 140, which is located at the proximal end of the body, and inner lumen flush 122. A microcatheter 130 may be inserted through the proximal end of handle body 100B. The hemostasis valve 140 may be adjustable to hold microcatheter 130 in place. Inner lumen flush 122 may be connected to the lumen of inner shaft 120. Inner lumen flush 122 may be positioned towards the proximal end of the handle body 100B. The handle body 100B may also include thumb lever 115, which may be positioned towards the distal end of the handle body 100B.

With reference to FIG. 1A and FIG. 1B, the handle body (100A/100B) is configured with a lumen through which outer shaft 110 passes. Outer shaft 110 in turn is configured with a lumen through which inner shaft 120 passes. The one or more microcatheter 130 (as shown, e.g., in FIG. 1B) in turn passes through the inner shaft 120. The outer shaft 110, inner shaft 120, and microcatheter 130 may be slideably operable independently of each other. Thus, the inner shaft 120 may telescope in and out of the outer shaft 110 and the one or more microcatheter 130 may telescope in and out of the inner shaft 130. Furthermore, when one or more guidewires 132 is used in conjunction with microcatheter 130, the one or more guidewires 132 may be slideably operable independently of the outer shaft 110, inner shaft 120, and microcatheter 130. The one or more guidewires 132 may telescope in and out of the microcatheter 130.

The outer shaft 110 may be configured to act as a sheath. The inner shaft 120 and outer shaft 110 may be flexible and roughly of cylindrical shape and/or having a generally circular transvers cross-section. The handle body may be made of a rigid plastic material.

In one embodiment, the apparatus includes an outer shaft having a lumen, an inner shaft having a lumen, a microcatheter having a lumen, a scaffold structure and one or more guidewires. The outer shaft is configured to allow passage of the inner shaft through lumen of the outer shaft. The microcatheter passes through the lumen in the inner shaft and the one or more guidewire in turn pass through the lumen of the microcatheter shaft. The scaffold structure may be attached to the inner shaft towards or on the distal end of the inner shaft 120.

The scaffold structure provides anchoring support and may be non-occlusive, allowing blood flow to collateral and branch vessels. While the scaffold structure may be self-expanding, scaffold structures suitable for use in the devices of the invention are not limited to self-expanding scaffold structures. Preferably, the scaffold structure has a broad working range (i.e., one size fits all). The scaffold structure may also be tailored for the specific intended uses. The scaffold structure may alone, and/or in combination with other structures and/or features to position the catheter device in the artery and to position the one or more microcatheters substantially centered in the middle of the scaffold/artery.

The scaffold structure may have a centering element, e.g., a mechanism to support an internal lumen and/or catheter or microcatheter away from the vessel wall. The scaffold structure may be atraumatic to the vessel wall thereby requiring minimal hoop strength to maintain position. The scaffold structure is configured to re-sheath to facilitate withdrawal and can be employed multiple times. The scaffold may be removable and used temporarily for reliable positioning and centering, preferably, for positioning and centering of a microcatheter. The scaffold preferably is of a quality and construction for being temporarily deployed in the vasculature, for anchoring in the vasculature, for being removable from the vasculature and/or for being redeployed in the vasculature. The scaffold, although it may be of implantable quality and construction, it is not intended to be used as an implant or an implantable device that remains in the vasculature after use, for example, for crossing a lesion.

Figure 2A:
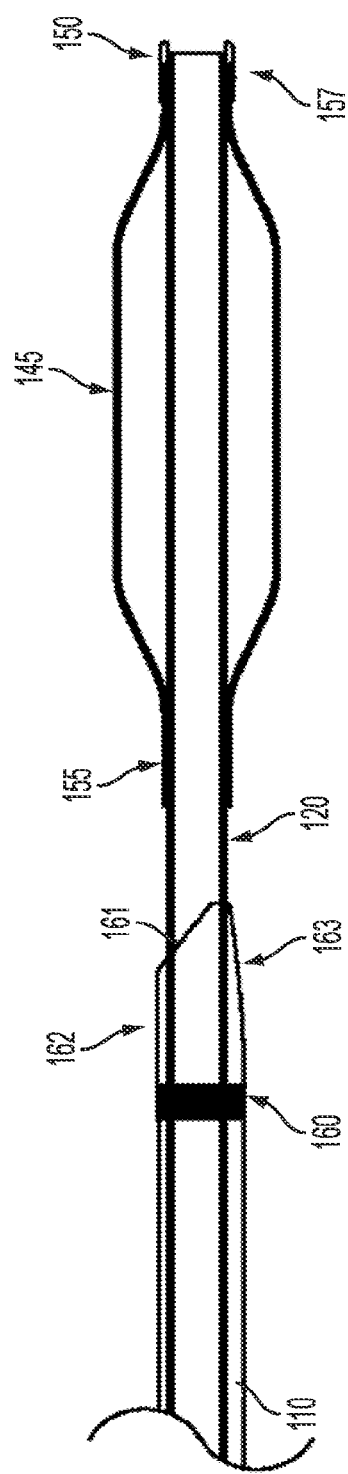
FIG. 2A is a partial cross-sectional view of a distal end of a catheter apparatus in accordance with principles of the invention.

FIG. 2A shows a partial cross-sectional view of the distal design of a catheter apparatus according to one embodiment of the invention in its expanded state without a microcatheter. In one embodiment, the catheter apparatus of FIG. 2A includes handle body 100, which may be configured as illustrated above. In another embodiment, the catheter apparatus of FIG. 2A may not include handle body 100. The catheter apparatus may further include one or more microcatheters.

With reference to FIG. 2A, the distal design of the catheter apparatus includes an inner shaft 120 having a lumen, a distal opening and a distal end; an outer shaft 110 having a lumen, a distal opening and a distal end for passing the outer shaft 110 over the inner shaft 120 and a self-expandable scaffold 145 disposed towards or attached towards the distal end of the inner shaft 120. Preferably, the self-expandable scaffold structure 145 has a proximal end 155 and distal end 157. The apparatus may also have a distal tip 150. Distal tip 150 may vary in construction and hardness. In one embodiment, distal tip 150 may be soft. The distal tip 150 is attached to the scaffold structure 145. Preferably, the scaffold structure 145 is self-expanding. FIG. 2A shows scaffold 145 in an expanded position. The proximal end 155 of self-expandable scaffold 145 is disposed or attached (e.g. fixed) to the inner shaft 120, as shown, at a distal end of the inner shaft 120. Preferably, the distal end 157 or distal tip 150 of the scaffold 145 is not attached to the inner shaft 120, for example, the scaffold 145 is slidably attached to the inner shaft 120. Although, if desired the distal tip 150 may be attached to the outer shaft depending on the scaffolding and use of the device. The distal end 157 of the scaffold 145 may be crimped. The distal end 157 of scaffold structure 145 may be held in place by a ring, for example, of the types and kinds described and shown with respect to FIG. 2B, at reference numeral 170, without being fixed to the inner shaft 120 thereby allowing the ring to move and slide back and forth longitudinally. The ring 170 can slide relative to shaft 120. In an alternate embodiment, the distal tip of the scaffold may be folded over so that the distal tip may be oriented toward the proximal end 155 as described herein and shown in FIGS. 6 and 11B. The ring 170 may be slid over the folded over distal tip of this alternate embodiment, although not shown in the figures.

The outer shaft 110 may include position detection marker 160 towards the distal end of the outer shaft. The detection marker 160 may be a radio-opaque marker band. Markers can also be provided elsewhere, for example, markers can be provided on the inner shaft 120 and/or the microcatheter 130.

The outer shaft may also have distal tip 162 on the distal end of the outer shaft 110. The distal tip 162 of the outer shaft 110 may be beveled and/or rounded. As shown, the end of the outer shaft 110 is beveled as shown at 161 and is curved at 163. This may aid in the delivery and/or positioning of the system. For example, this configuration may aid in preventing deflection away from the fibrous cap towards the adventitial layer, and thereby may aid in the prevention of the device entering a false lumen. Alternatively, the distal tip of the outer shaft may be tapered, beveled, round or combinations thereof.

The outer shaft 110 may have a hydrophilic coating on the distal end. The outer shaft may have a diameter of about 0.062 inches. The lumen of the outer shaft may have a diameter of about 0.054 inches. When in use, the outer shaft translates to cover and uncover self-expandable scaffold structure 145. As such, the scaffold can exit out of and be refracted into outer shaft 110.

The inner shaft 120 may be in a fixed position relative to handle body 100. The inner shaft 120 may be in tubular shape to allow effective communication to a distal vessel. The minimum diameter of the lumen of the inner shaft 120 may be about 3 French. Alternatively, the diameter of the inner shaft may be from about 0.045 to about 0.050 inches. The inner shaft may be configured to be compatible with one or more microcatheters and/or guidewires. In one embodiment, the inner shaft may be configured to be compatible with a guidewires about 0.038 inches in diameter. The inner shaft is preferably approximately centered relative to the self-expandable scaffold structure 145.

Preferably, the inner shaft 120 is configured to be flexible, lubricious, and kink-resistant. In one embodiment, the inner shaft 120 is configured to be compatible with a microcatheter, which is compatible with guidewires about 0.014 to about 0.018 inch. The inner shaft is preferably affixed to a proximal handle (such as, e.g., handle body 100). But, inner shaft 120 may not be fixed so it can be moved independently as well.

The outer shaft 110 and inner shaft 120 may be slideably operable independently of each other. Thus, the inner shaft may telescope in and out of the outer shaft. Furthermore, the lumens of the inner and outer shaft may be configured to accommodate one or more guidewires. The one or more guidewires may also telescope independently from the outer and inner shaft.

Figure 2B:
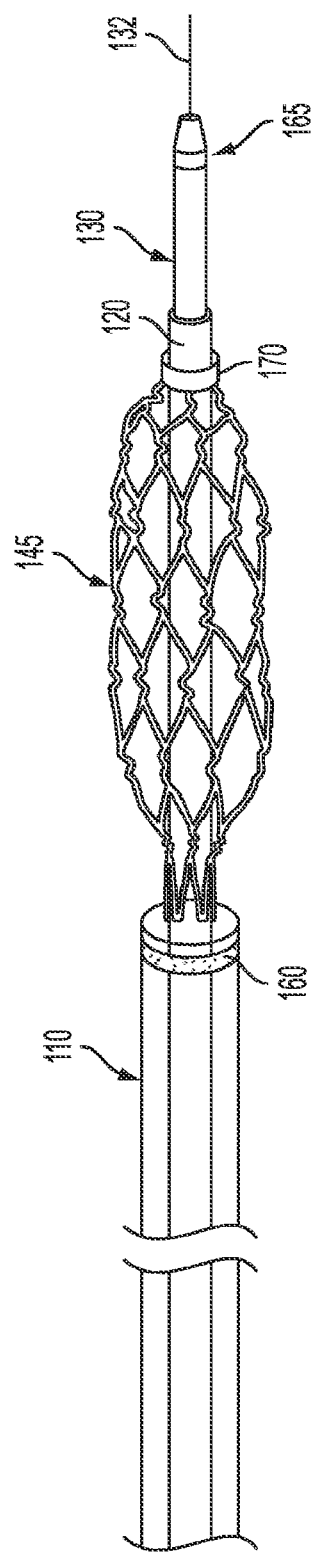
FIG. 2B is a view of a distal end of a catheter apparatus in accordance with principles of the invention.

FIG. 2B shows a view of the distal design of a catheter apparatus according to one embodiment of the invention in its expanded state with the microcatheter 130 in place. In one embodiment, the catheter apparatus of FIG. 2B includes handle body 100 as illustrated above. In another embodiment, the catheter apparatus of FIG. 2B may include other proximal apparatus and/or handle(s), as discussed further below.

The catheter apparatus includes a microcatheter 130 having a lumen, a distal opening and a distal end; one or more microcatheter guidewires 132 for passing through the lumen of the microcatheter 130; an inner shaft 120 having a lumen, a distal opening and a distal end for passing the inner shaft 120 over the microcatheter 130; an outer shaft 110; and a self-expandable scaffold 145 structure disposed towards or attached towards the distal end of the inner shaft 120.

As shown in FIG. 2B, outer shaft 110 has a lumen through which inner shaft 120 passes. Inner shaft 120 in turn has a lumen through which microcatheter 130 passes. The microcatheter also has a lumen through which one or more guidewires passes. In a preferred embodiment, only one guidewire 132 passes through the lumen of the microcatheter. The outer shaft 110, inner shaft 120, and microcatheter 130 may be slideably operable independently of each other. Thus, the inner shaft 120 may telescope in and out of the outer shaft 110 and the microcatheter 130 may telescope in and out of the inner shaft 120. Furthermore, one or more guidewire 132 may telescope independently of the inner shaft 120, outer shaft 110, and/or microcatheter 130. The microcatheter 130 and guidewire 132 may be advanceable as a group. Alternatively, the microcatheter 130 and guidewires 132 may be individually advanceable.

Preferably, the proximal end of the scaffold structure is attached to the inner shaft 120. The proximal end of the scaffold may be physically attached to the inner shaft 120. The proximal end of the scaffold may be held in place by a biologically acceptable glue or a fitting. The fitting would slide over the proximal end of the scaffold and hold it in place. The fitting, as shown, may include a ring 170 positioned around the distal end of the scaffold structure 145 without attaching or fixedly securing the scaffold structure 145 to the inner shaft 120. Thus, the distal end of the scaffold is slidable.

The outer shaft 110 may include position detection marker 160 towards the distal end of the outer shaft. In one embodiment, the position detection marker 160 is a marker band such as, e.g., a radiopaque marker. The distal end of the outer shaft 110 may be beveled and rounded.

The microcatheter 130 may also include one or more position detection markers 165. The position detection marker 165 may be a marker band such as, e.g., a radiopaque marker. The inner shaft may also include markers, not shown.

The microcatheter 130 may include a tapered tip at the distal end. The tip may be soft. Alternatively, the hardness may vary. The microcatheter 130 is independently movable from the inner shaft 120 and may be removable. Preferably, the microcatheter 130 translates independently within the lumen of inner shaft 120. The microcatheter 130 has a lumen through which a one or more guidewires may pass. The microcatheter 130 may have a lumen with an internal diameter of about 0.017 to about 0.021 inches. The microcatheter may have an outer diameter of about 2.1 French at the tip and an outer diameter of about 2.5 French proximal to the taper. Furthermore, the microcatheter may be highly flexible and may have a low profile (<3 French) as well as a soft distal tip.

The microcatheter 130 can advance beyond the distal end of the inner shaft 120 to support a guidewire 132, which is advanced through the lesion. Thus, the microcatheter 130 is able to provide structural rigidity and/or support to the guidewire by protecting it from unnecessary bending. In a preferred embodiment, the microcatheter is harder and/or has more column strength than the guidewire. The reliably centered microcatheter and guidewire passing through the microcatheter allows for targeted central access to the lesion and/or occlusion. The ability to translate both the microcatheter and/or the guidewire together and independently allows for controlled variable engagement with the lesion and/or occlusion. The differing hardness/softness between the microcatheter and the guidewire also allows for varied engagement with the lesion and/or occlusion.

The microcatheter 130 also may serve as an extension to the scaffold. The microcatheter may be extended distally beyond the distal end of the deployed/anchored scaffold, yet the microcatheter remains reliably centered as a result of the scaffold. The centered extended microcatheter extends the centering capability of the system distally from the scaffold to center the guidewire further distally.

The components of the catheter apparatus of the invention have varying degrees of rigidity. Preferably, the rigidity and/or support increases going from the microcatheter guidewires 132 to the microcatheter 130. The rigidity and/or support also increases going from the microcatheter 130 to the inner shaft 120. The rigidity and/or support further increases going from the inner shaft 120 to the outer shaft 110. The handle body 100 has the highest degree of rigidity. In other words, in a preferred embodiment, the microcatheter is more rigid and has more column strength than the guidewire. The inner shaft is more rigid and has more column strength than the microcatheter, and therefore the guidewire, too. The outer shaft is more rigid and has more column strength than the inner shaft.

The outer shaft, inner shaft, and microcatheter may be made of a flexible plastic material or any other substance or materials as appropriate to accommodate curves, bends and tortuosity in the vasculature, for example.

The position detection marker 160 and marker 165 may be simple radiopaque markers. With radiopaque marking, users may improve their ability to identify the location of the distal end of the catheter and microcatheter during a procedure.

Figure 2C:
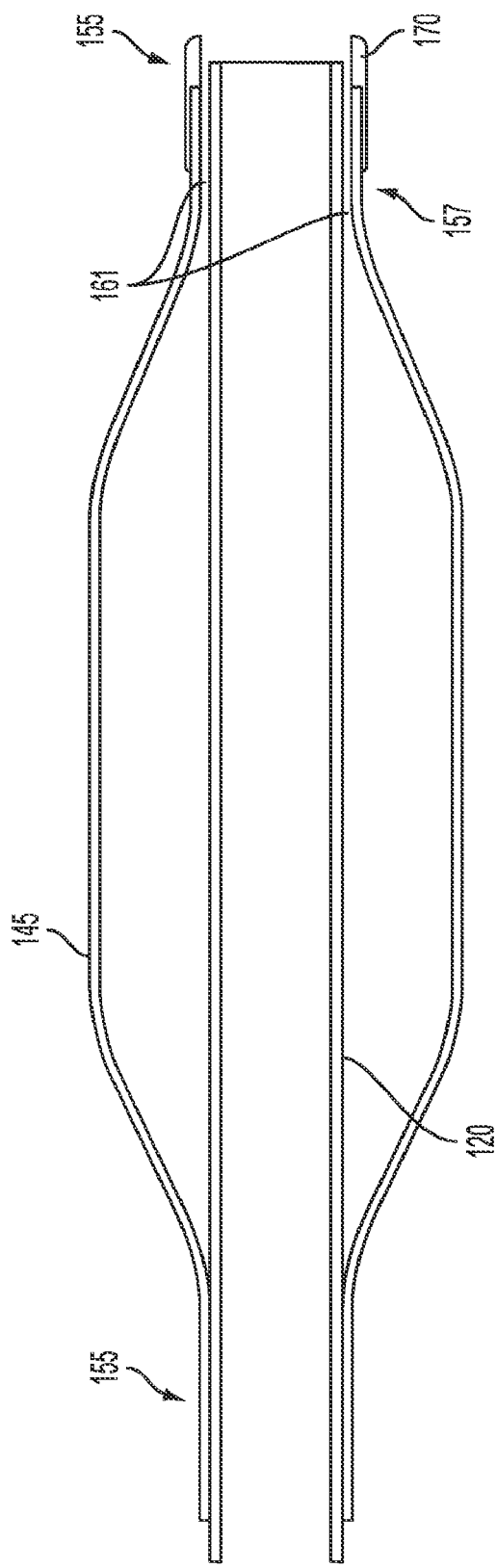
FIG. 2C is a cross-sectional view of the self-expandable scaffold structure at the distal end of a catheter apparatus in accordance with principles of the invention.

FIG. 2C is a partial view of one embodiment of the self-expandable scaffold 145 structure at the distal end of a catheter apparatus shown in FIG. 2A. With reference to FIG. 2C, the arrangement of expandable scaffold structure 145 on inner shaft 120 is shown. As discussed above, the inner shaft 120 has a lumen through which microcatheter may pass. The proximal end 155 of self-expandable scaffold 145 is disposed or attached (e.g., fixed) to the inner shaft 120. The distal tip 150 is disposed or attached (e.g., fixed) to the distal end 157 of scaffold 145. As shown, the distal end 157 and distal tip 150 are not attached to the inner shaft 120. Gap 161 separates the scaffold structure 145 from the inner shaft 120. In one embodiment, the distal end 157 and/or distal tip 150 are held in place by a ring 170 while maintaining gap 161. The ring 170 is mounted on distal end 157. In an alternate embodiment, not shown in FIG. 2C, the distal tip 150 may be folded over so that the distal tip 150 is oriented towards the proximal end 155 and the ring 170 may be slid over the folded over distal tip.

Scaffold structure 145 may be self-expandable. The proximal end 155 of the scaffold structure 145 is preferably physically attached to the inner shaft 120, preferably, fixedly attached and, more preferably, fixedly attached to prevent any substantial movement relative to shaft 120. As discussed above, the proximal end of the scaffold may be held in place by a biologically acceptable glue or a fitting. The scaffold is towards the distal end of the inner shaft 120. In one embodiment, the proximal end 155 may be attached to the inner shaft 120. In one embodiment, the scaffold structure 145 is configured such that outer shaft 110 can slide over the self-expandable scaffold structure 145 and thereby collapse the scaffold. In one embodiment, the self-expandable scaffold structure 145 is retractable into the outer shaft 110.

The scaffold structure 145 creates a substantially tube-like and/or cylindrically-shaped structure. It is configured in such a way that the inner shaft 120 (and therefore microcatheter 130 and guidewire) pass through approximately the center of the scaffold. Preferably, the self-expandable scaffold structure is substantially cylindrical. In one embodiment, the inner shaft 120 (and therefore microcatheter 130 and guidewire) passes through the center of the scaffold. In another embodiment, when in operation, the inner shaft 120 (and therefore microcatheter 130) passes through the center of the scaffold and the center of the vasculature. This configuration allows for reliable positioning in the vasculature for center access to the CTO. In particular, the distal end opening of the inner shaft and the distal end opening of the microcatheter are positioned, disposed, and/or centered on the central longitudinal axis of the anchored scaffold, therefore providing reliable central access to the lesion and/or CTO. The scaffold, inner shaft and microcatheter in various combinations, reliably center the system for centered positioning of the guidewire and for translation of the shaft, microcatheter and guidewire to cross the lesion and/or CTO at the center.

The self-expandable scaffold structure 145 may be in a cellular configuration. In another embodiment, the scaffold structure may be configured as a lattice. Various patterns may be used in accordance with the principles of the invention. The self-expandable scaffold structure 145 may preferably be configured to be non-occluding thereby allowing blood to flow through during the procedure. The vasculature is not occluded with the system described herein. In another configuration, the scaffold structure may be composed of braided wires. Nitinol and/or stainless steel may be incorporated into the self-expandable scaffold structure 145. Nitinol is an illustrative example of a shape memory alloy. Other shape memory alloys or other similar substances may be used. Generally, after a sample of a shape memory alloy has been deformed from its original crystallographic configuration, the shape memory alloy regains its original geometry by itself. This property of shape memory alloys may allow for expansion of the self-expandable scaffold structure 145 after telescoping from the outer shaft 110. The nitinol and/or stainless steel self-expandable scaffold structure 145 may create a stent-like mesh.

A self-expanding polymer may fill the interior portion of self-expandable scaffold structure 145. In an initial configuration, the self-expanding polymer may be in a compressed state. As the scaffold structure slideably expands by movement of the inner shaft, the self-expanding polymer may expand as well. The self-expanding polymer may expand by absorbing moisture or blood from within the vasculature or through other expansion mechanisms.

In one embodiment, the scaffold is about 20 mm in length when compressed. When fully expanded the scaffold length may decrease. In one embodiment, the scaffold may be incrementally expandable in increments from about 2.0 mm to about 5.0 mm. The scaffold may position the inner shaft 120 and microcatheter 130 so that they are approximately centered relative to the chronic total occlusion.

The catheter apparatus may further include one or more guidewires. The lumen of the inner shaft, the outer shaft, or both may be configured to accommodate guidewires. The one or more guidewires may be passed through the chronic total occlusion using the system described herein.

The catheter apparatus may be withdrawn from the vasculature while leaving the one or more guidewires in place (including the one or more guidewires to pass through the lumen of the microcatheter). The scaffold structure may be repositioned repeatedly until a suitable site for passing the guidewire and/or microcatheter through the chronic total occlusion is found. According to some embodiments discussed further below, one or more of the guidewire(s), microcatheter, and inner shaft, including the scaffold, may be withdrawn from the vasculature while leaving the outer shaft in place. Thus, guidewires, the inner shaft and scaffold, microcatheters, or other instruments or catheters may be inserted into the vasculature through the outer shaft that was left in place. In this way, the outer shaft may be used as a guide catheter.

Standard off-the-shelf or customized guidewires may be used. For example, in addition to traditional guidewires, embodiments of the present invention may be used with guidewires including, but not limited to, steerable, hydrophilic, Teflon-coated, heparin-coated, ball-tip, J-tip, spiral tip, angulated wire and others.

Embodiments of the present invention may deliver energy via the microcatheter through radio frequencies and/or lasers. Furthermore, other types of energy may be delivered such as direct conductive heat energy, infrared or other types of energy that may be useful in particular applications. Various types of microcatheters and/or delivering energy via microcatheters may allow for various types of treatments.

The external diameter of a catheter apparatus of the present invention may allow passage through a standard guide catheter. The outer surface of a catheter apparatus of the present invention may be coated with hydrophilic material to allow easier passage through the guide catheter. With alternate dimensions, a catheter apparatus of the present invention may be used in peripheral vessels. In this situation, a guide catheter may not be necessary to insert the device into the vasculature.

The conversion of the scaffold 145 from its unexpanded to expanded state creates a reasonably stable platform for advancing the inner shaft, microcatheter and one or more guide wires through the center of the occlusion. The expanded scaffold may be substantially cylindrical or a hollow tube. In certain embodiments, the activated scaffold 145 may achieve other forms as well.

To achieve the expanded state shown in FIGS. 2A and B, the collapsed catheter apparatus is expanded. In this collapsed configuration, the self-expandable scaffold structure 145, which is attached to inner shaft 120 towards or on the distal end, is positioned inside the outer shaft 110 between outer shaft 110 and inner shaft 120. Microcatheter 130 is positioned inside the inner shaft 120 when desired and can be preloaded. The guidewire in turn is positioned inside the microcatheter when desired and can be preloaded. The collapsed catheter apparatus may be advanced over one or more guidewires with the outer shaft in place to constrain the self-expanding but unexpanded self-expandable scaffold structure 145. The outer shaft 110 may cover the self-expandable scaffold structure 145. When the unexpanded scaffold structure is properly positioned, the outer shaft may be retracted. As the outer shaft 110 is retracted, the unexpanded self-expandable scaffold structure 145 expands to a substantially cylindrical or hollow tube shape and may flare out. During the expansion process, the unexpanded scaffold structure may self-expand to assume a larger diameter to roughly approximate the diameter of a vasculature. The microcatheter 130 may telescope along with the inner shaft 120 or separately.

The outer shaft 110 may be retracted to a stop point. The stop point may prevent over-retraction of the outer shaft 110. Maintaining the position of the outer shaft 110 at the stop point may facilitate re-sheathing (i.e. collapsing) the self-expandable scaffold structure 145.

The catheter devices and systems in accordance with the principles of the invention allow for gentle expansion to the artery wall/gentle engagement with the vasculature by anchoring of the scaffold, scaffold positioning of the shaft(s) and/or microcatheter, the individually independently telescoping outer shaft, inner shaft and microcatheter, and the differing rigidity/softness relationships among the scaffold, shaft(s) and microcatheter. In particular as the self-expandable scaffold expands and presses against the walls of the vessel to approximately center the inner shaft relative to occlusion. Preferably, the distal opening of the inner shaft is positioned at the center of the CTO in the vasculature. Preferably, the distal opening of the microcatheter is positioned at the center of the CTO in the vasculature. The scaffold holds the device in place while the one or more catheters, preferably microcatheters, and/or guidewires are able to translate. The scaffold preferably anchors in close proximity to the CTO so that the microcatheter and the guidewire contact the CTO at the CTO's center. Furthermore, the devices of the invention are also unique in that the self-expandable scaffold structure is preferably non-occluding allowing blood to flow through.

Thus, another embodiment of the invention is a method of treating vasculatures such as, e.g., chronic total occlusion of a vasculature by providing a catheter apparatus of the invention in its collapsed state, positioning the collapsed catheter apparatus close to the site of occlusion, expanding the collapsed catheter apparatus such that the device expands in the occlusion, telescoping the inner shaft and/or microcatheter and advancing the guidewire through the occlusion. In particular, the devices of the invention are prepared for use by collapsing the scaffold structure. The self-expandable scaffold structure may be collapsed by sliding the outer shaft over it by actuating a thumb lever to retract the scaffold. In some embodiments, the scaffold structure may be collapsed by sliding the outer shaft over it by moving the proximal end of the out shaft relative to the proximal end of the inner shaft. The tip of the device is delivered to the target location. The outer shaft is then retracted, allowing the self-expanding scaffold structure to expand naturally up to the vessel diameter. Once the self-expandable scaffold is expanded, the inner shaft is centered inside the self-expandable scaffold and, therefore, the inner shaft is centered in the vessel. This allows for reliable central positioning relative to the CTO, lesion, and/or fibrous cap, thereby providing the microcatheter and guidewire optimal access, control, alignment, and reliability to cross and/or pass the lesion.

Generally, after crossing a chronic total occlusion with a guidewire, the catheter apparatus may be resheathed and removed from the vasculature. The guidewire and/or microcatheter may be left in position. In some embodiments, the outer shaft may be left in position after removal of one or more of the guidewire, microcatheter, and inner shaft.

Figure 3:
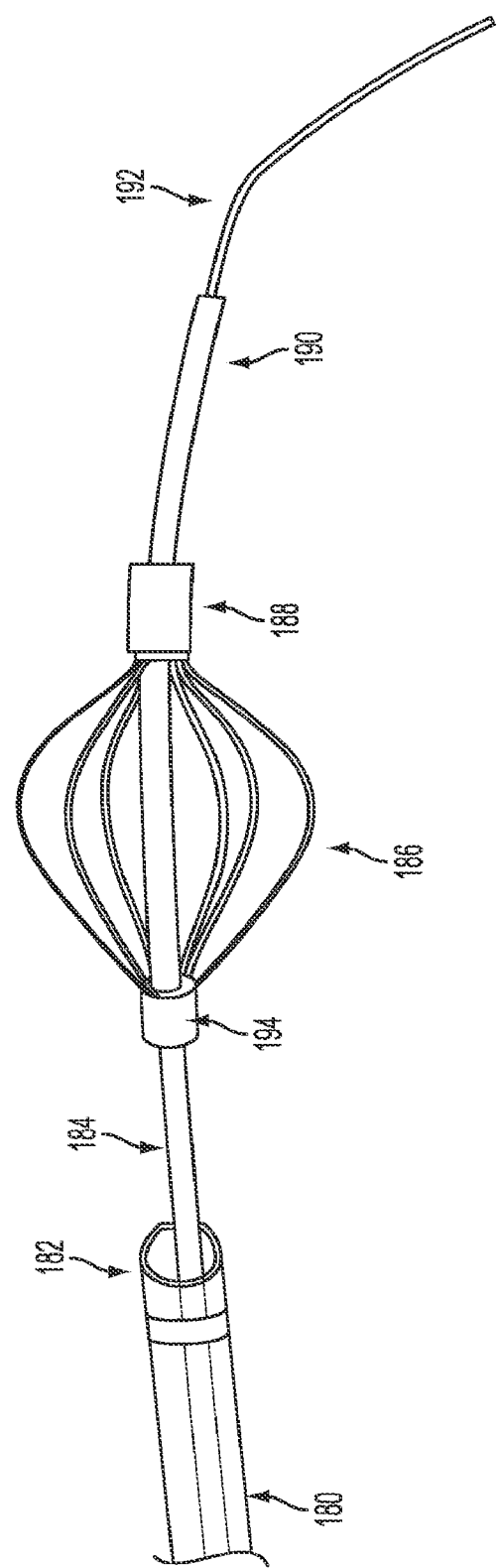
FIG. 3 is a view of a distal end of a catheter apparatus in accordance with principles of the invention.

The positioning of the guidewire reliably in the center may optimize the force of the guidewire when engaged with the fibrous cap of the chronic total occlusion. The mass, rigidity, hardness, softness, strength and/or construction of the catheter apparatus, shaft(s) and/or the microcatheter, and/or combinations thereof, may provide additional support for the microcatheter and/or guidewire and prevents off-axis, i.e., lateral, displacement of the microcatheter and/or guidewire in the vasculature. Concentric placement of the microcatheter and/or guidewire may allow for reliable central access to the fibrous cap despite the anatomy and/or tortuosity of the anatomy. FIG. 3 shows a view of the distal configuration of a catheter apparatus according to another embodiment of the invention in its expanded state. The distal configuration of the device includes outer shaft 180, an inner shaft 184, a self-expandable scaffold 186, a sleeve 188, a microcatheter 190, and a guidewire 192. The outer shaft has a lumen, a distal opening, and a tip 182 on the distal end. The inner shaft 184 also has a lumen, a distal opening, and a distal end. The microcatheter 190 also has a distal opening and a lumen. As is shown in FIG. 3, the device is flexible to allow the device to more through bends in arteries.

The outer shaft 180 is configured to allow passage of the inner shaft 184 through the lumen of the outer shaft. The inner shaft 184 is configured to allow passage of the microcatheter 190 through the lumen of the inner shaft. The microcatheter 190 is configured to allow passage of guidewire 192 through the lumen of the inner shaft. In one embodiment, the device includes one guidewire although multiple guidewires may be used serially or simultaneously.

The distal end of the outer shaft 180 has a distal tip 182. The distal tip 182 may be configured with a beveled end and/or a bend. For example, the outer shaft 180 may have two parallel longitudinal axes running from opposing sides of the lumen of the outer shaft 180. One longitudinal axis passes through the distal tip 182 and the other longitudinal axis passes through the opposite end of the outer shaft 180. The distal end of the outer shaft 180 may be tapered toward the one longitudinal axis.

The self-expandable scaffold 186 is attached to the inner shaft at the proximal end 194. Preferably, this attachment is fixed and not substantially moveable or slidable.

The inner shaft 184 may have a sleeve 188 attached towards the distal end of the inner shaft 184. Sleeve 188 is placed over the distal end of the scaffold structure 186 without fixedly attaching the scaffold structure 186 to the shaft 184. Sleeve 188 is preferably slidable relative to the inner shaft 184. Preferably, expansion of the self-expandable scaffold structure 186 pushed up against sleeve 188 such that it holds the sleeve 188 in place.

Figure 4:
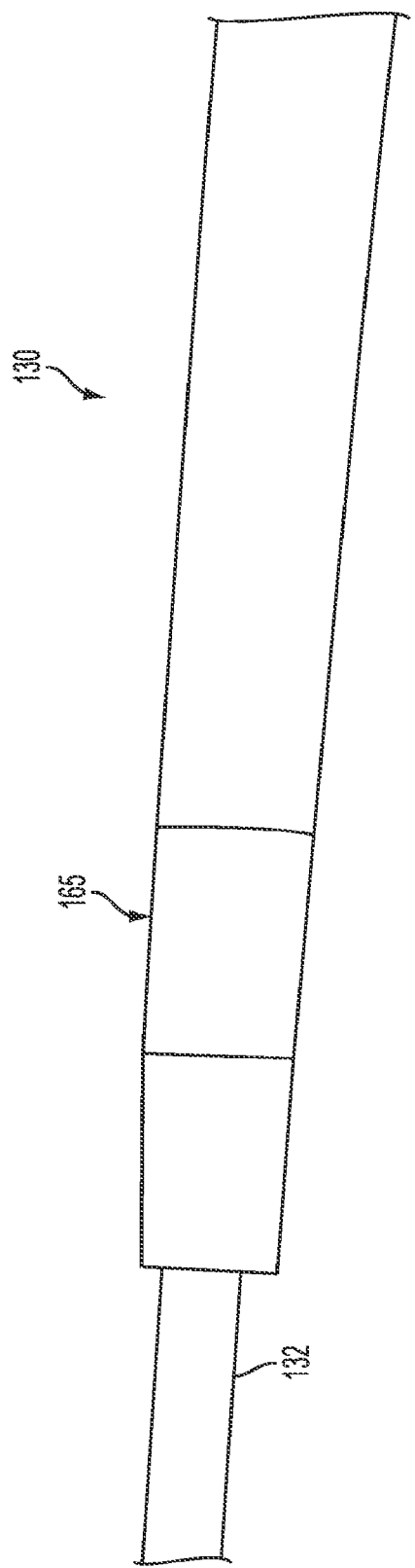
FIG. 4 is a view of a distal end of microcatheter in accordance with principles of the invention.

Various microcatheters may be used with the devices of the invention. FIG. 4 shows a distal end of a microcatheter 130 that may be used with the devices of the invention. Specifically, microcatheter 130 is shown with optional position detection marker 165. In certain embodiments, the microcatheter may have a single lumen. For example, as shown in FIG. 4, guidewire 132 may pass through the single lumen of microcatheter 130. In certain embodiments, the lumen may be about 0.017" in diameter. The microcatheter 130 may have a stainless steel braid structure. The microcatheter 130 may also have a hydrophilic coating. In certain embodiments, the microcatheter 130 may have an ultra-low profile. Preferably, the microcatheter 130 may be highly flexible and/or trackable (via, e.g., the use of a radiopaque marker band). While the microcatheter 130 may be highly flexible, in certain embodiments, the microcatheter is more rigid than the guidewire. Thus, the microcatheter 130 may provide additional support for the guidewire. The tip of the microcatheter 130 may be tapered. In one embodiment, the microcatheter 130 may have a soft, tapered tip. A microcatheter with a soft, tapered tip may be used for a coronary vasculature. In another embodiment, the microcatheter 130 may have a stiffer, tapered tip. A microcatheter with a stiffer, tapered tip may be used for use in a peripheral vasculature (e.g., below the knee). In one embodiment, the microcatheter 130 may have 2.7 F body and 1.7 F tip. The length of the microcatheter 130 may be about 150 cm, alternatively about 160 cm.

Figure 5:
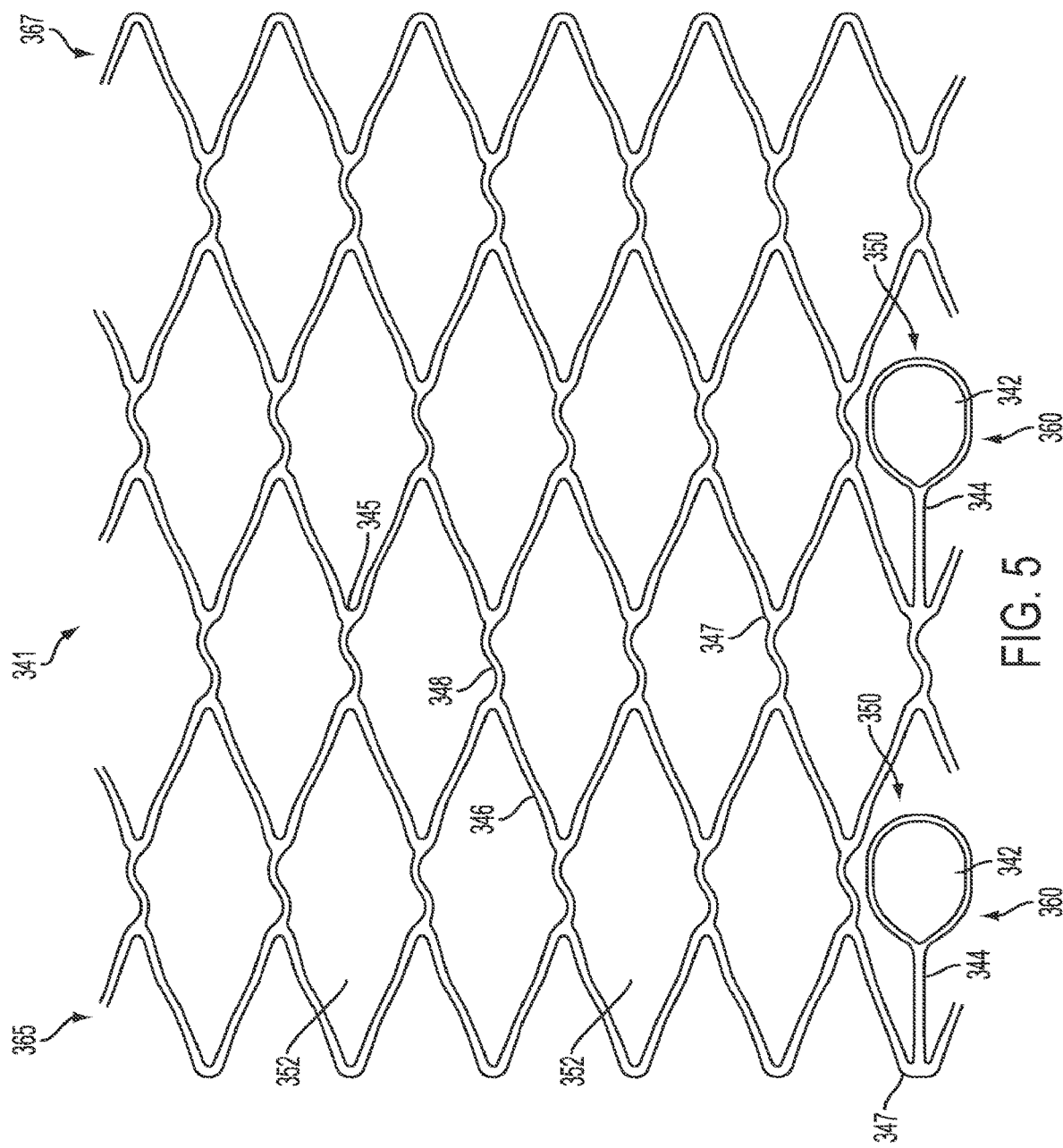
FIG. 5 is an unwrapped view of one embodiment of a scaffold of a catheter apparatus in an expanded state in accordance with principles of the invention.

FIG. 5 shows an unwrapped view of an embodiment of a scaffold in an expanded state in accordance with principles of the invention. Specifically, FIG. 5 shows a scaffold structure, which includes cells and connectors. The connectors project inward. While FIG. 5 shows a dual loop embodiment, which contains two loops (e.g., a pair of loops), the number of loops may vary.

FIG. 5 shows one embodiment of a configuration of a self-expandable scaffold structure 341, which is utilized in a similar manner to self-expandable scaffold structure 145. (See also, FIGS. 8A-9D, for example, and related description.) The expandable scaffold structure has a central longitudinal axis and may be non-occluding. The self-expandable scaffold structure 341 (when in its wrapped configuration) is substantially cylindrical, but is shown flat and has a proximal end 365 and a distal end 367. The connectors 360, including, as shown, a pair of connectors may be in the form of a loop. Connectors 360 are located in a pair with one at the proximal end 365 and the other in the distally adjacent cell. The connectors 360 include a loop 342 and a loop support 344. The loops 342 may be located at strut intersections 347. Loop supports 344 may couple the loops 342 to strut intersections 347. The loop supports 344 may be tapered to reduce stress on the apparatus. The loop supports 344 may also be flexible. The scaffold further includes struts 346, linking strut intersections 347, and connectors 348. The struts 346 may be connected to connectors 348 at linking strut intersections 347 or at strut intersections 345 if loops are present. A connection between two struts 346 and two connectors 348 via either two strut intersections or peaks and valleys 347, 345 or one strut intersection 345 and one strut intersection 345 creates a closed cell 352 or a closed cell 350. A closed cell 350 includes a loop, while a closed cell 352 does not contain a loop. The closed cells 350 and 352 create the scaffold. The number of cells may vary. In one embodiment, the scaffold contains two closed cells 350 and the remaining closed cells are closed cells 352.

When in a cylindrical shape attached on an inner shaft, the loops 342 may project inwardly from the cylindrical plane of the scaffold such that the inner shaft is positioned approximately in the center of self-expandable scaffold structure 341. In one embodiment, the loops 342 project inwardly from the cylindrical plane of the scaffold and the inner shaft passes through the loops such that the inner shaft may positioned in the center of self-expandable scaffold structure 341. The loops 342 center the inner shaft along a longitudinal axis of the device. The inner shaft is also positioned in the center of the chronic total occlusion when in use. The loops may be circular, oval oblong or any additional shape, including, but not limited to closed shapes, to position the inner shaft in the center of the self-expandable scaffold structure. Alternative numbers and configurations are possible.

The self-expandable scaffold structure 341 shown in FIG. 5 may be made of nitinol or another shape-memory material. The loop connectors 348 may also be made of nitinol or another shape-memory material.

With reference to the embodiment of the self-expandable scaffold structures shown in FIG. 5, when the outer shaft is withdrawn from around the self-expandable scaffold structure, the self-expandable scaffold structure may expand to an expanded state. The outer shaft may be partially or completely withdrawn from the expandable support structure. The inner shaft passes through loops 342 so during the expansion of self-expandable scaffold structure, as the scaffolding expands, the loop supports connect the scaffold with the loops (loops 342) that are disposed around the inner shaft causing the connectors 360 to project/move/extend inward from the cylindrical plane of the self-expandable scaffold structure to hold the inner shaft in an approximately centered position within self-expandable scaffold structure. As such, the inner shaft may be disposed and/or remain approximately centered in the scaffold during expansion and compression of self-expandable scaffold structure. Upon completion of a procedure, the self-expandable scaffold structure may be compressed and withdrawn from the vasculature. The outer shaft may be slid distally over the self-expandable scaffold structure. Preferably, no parts of the catheter apparatus extend outside of the cylindrical plane of the compressed self-expandable scaffold structure in the compressed state to facilitate withdrawal of the catheter apparatus.

Figure 6:
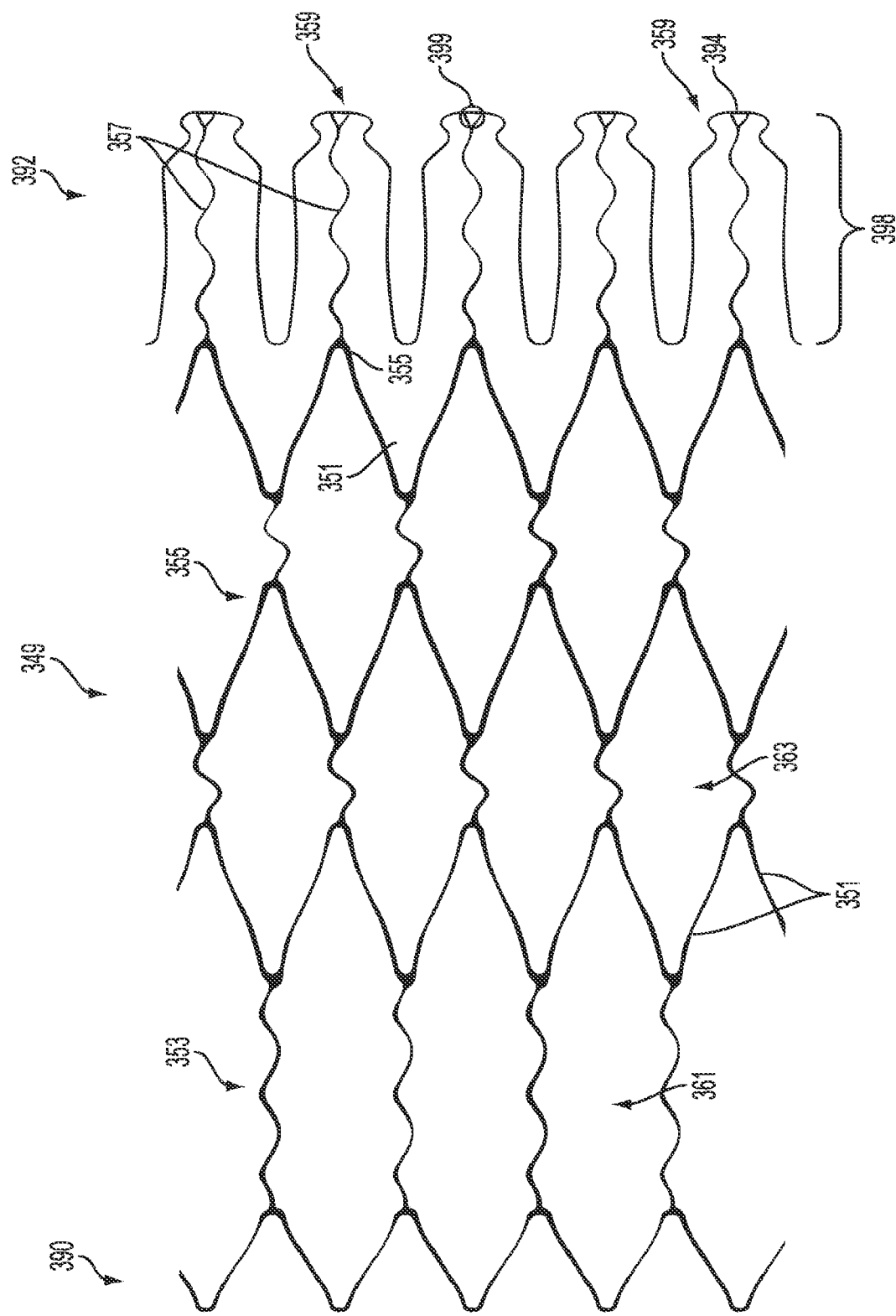
FIG. 6 is an unwrapped view of an embodiment of a scaffold including loop members in a partially expanded state in accordance with principles of the invention.

FIG. 6 shows another embodiment of a self-expandable scaffold structure 349, which is used in a similar manner as self-expandable scaffold structure 145. Structure 349 is shown with a proximal end 390 and a distal end 392. The self-expandable scaffold structure 349 is substantially cylindrical. The scaffold is comprised of cells with a loop structure at the distal end of the structure. In particular, the scaffold includes struts 351 which may be connected to strut connectors 353 at strut intersections 355. The struts 351 when connected to strut connectors 353 form closed cells 361 and 363. The cells, in one embodiment, may be in approximately a honeycomb structure. The closed cells 361 and 363 create the scaffold. The number of cells in the scaffold may vary. The dimension of strut connector 353 may vary. In one embodiment, the dimension of the strut connectors varies depending on whether the self-expandable scaffold structure is expanded or collapsed. At the distal end 392 of the self-expandable scaffold structure 349, an attachment section 398 includes distal connectors 357 that may be connected to struts 351 at strut intersection 355. The distal connectors 357 may be connected to distal loop 359 via intersections 394. The distal connectors 357 may have a branched distal end 399. The distal connectors 357, distal loop 359, and intersections 394 may form a structure that when crimped down on the inner shaft may create a sphinctering effect. This sphinctering effect may hold the self-expandable scaffold in place at the attachment point (such as, e.g., a sleeve) on inner shaft while still allowing for sliding movement along the inner shaft. This can be accomplished also by inverting the section 398 as well. (See FIG. 11B for example.) In one embodiment, the scaffold structure may include such a configuration and/or loop network also at the proximal end.

The distal connectors 357 may have two branches at the distal end. Thus, each distal connector may be connected to distal loop 359 at two intersections 394. Preferably, the distal end is configured so that distal connectors 357 point inward towards the inner shaft. Thus, the distal loops also face inward thereby creating a sphinctering effect. This sphinctering effect, which aids in the positioning of the self-expandable scaffold structure relative to the inner shaft. Alternative numbers and configurations are possible. Due to the intrinsic properties of the scaffold such as, e.g., the sphinctering, the inner shaft remains positioned approximately in the center of self-expandable scaffold structure. Furthermore, inner shaft also remains approximately centered in the chronic total occlusion.

With reference to the embodiment of the self-expandable scaffold structure shown in FIG. 6, when the outer shaft is withdrawn around the self-expandable scaffold structure, the self-expandable scaffold structure may expand to an expanded state. The outer shaft may be partially or completely withdrawn from the expandable support structure. During the expansion of self-expandable scaffold structure, the section and/or loop network at the distal end 392 of the scaffold may create a sphinctering effect. The inner shaft may remain approximately centered during expansion and compression of self-expandable scaffold structure. Also, during the expansion the angle of the connectors 353 relative to the cells 361 and/or 363 may change. Similarly, during the expansion the angle of the distal connectors 357 relative to the distal loop 359 may also change. Upon completion of a procedure, the self-expandable scaffold structure may be compressed and withdrawn from the vasculature. The outer shaft may be slid distally over the self-expandable scaffold structure. Preferably, no parts of the catheter apparatus extend outside of the cylindrical plane of the compressed self-expandable scaffold structure in the compressed state to facilitate withdrawal of the catheter apparatus.

The self-expandable scaffold structure 349 shown in FIG. 6 may be made of nitinol or another shape-memory material. The strut connectors 353 and distal connectors 357 may also be made of nitinol or another shape-memory material.

Figure 7:
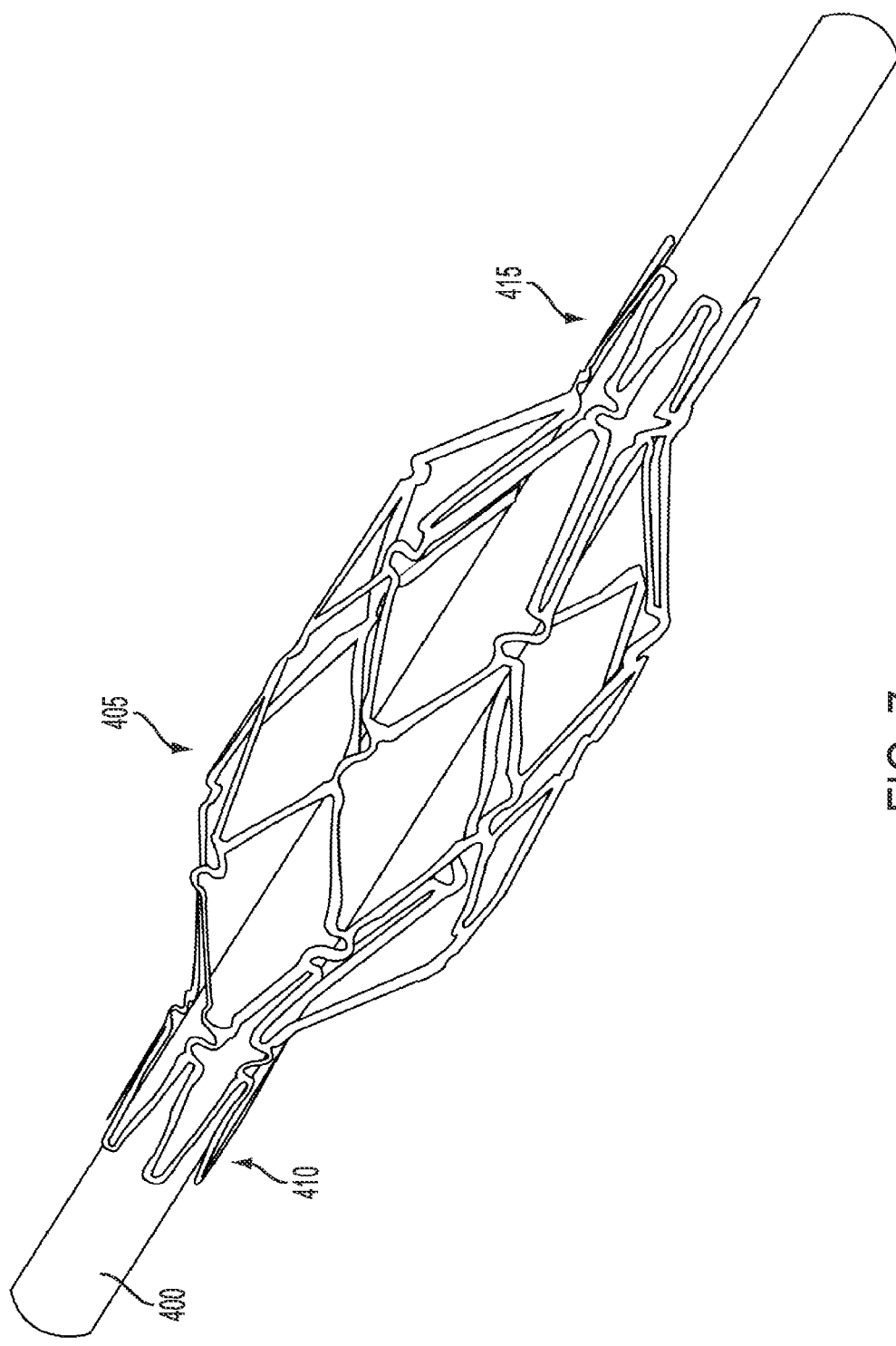
FIG. 7 is perspective view of another self-expanding scaffold in an expanded state positioned on a shaft of a catheter apparatus in accordance with principles of the invention.

FIG. 7 shows another embodiment of a self-expandable scaffold structure of the invention. FIG. 7 is a close-up view of a self-expandable scaffold structure 405 positioned on inner shaft 400. The scaffold structure 405 and inner shaft 400 are part of a catheter apparatus as described above (e.g., a catheter apparatus including an outer shaft, an inner shaft, a self-expandable scaffold, and a microcatheter). The scaffold structure includes proximal end 410 and distal end 415. The scaffold structure 405 may be attached to the inner shaft 400 via the proximal end 410, preferably, fixedly attached. The scaffold structure 405 may be held in place at the distal end 415 alone or with a sleeve (not shown) such that the scaffold structure is slideably along the shaft. The self-expandable scaffold structure 405 is cellular shape (such as, e.g., a honeycomb). The proximal end 410 and the distal end 415 of the scaffold remain crimped on the shaft while the main body of the scaffold expands.

Figure 8A:
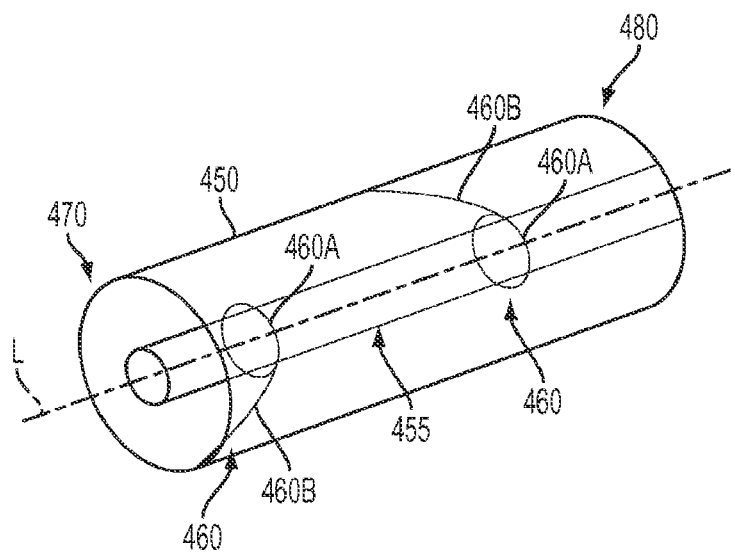
FIG. 8A shows a perspective view of an embodiment of a scaffold attached to a shaft in accordance with the principles of the invention.

FIG. 8A shows a perspective view self-expanding scaffold in its expanded state positioned on an inner shaft of a catheter apparatus in accordance with one embodiment of the invention. With reference to FIG. 8A, scaffold 450 is shown in an expanded and generally cylindrical form. Scaffold 450 includes a wall defining an interior space. Expanded self-expandable scaffold 450 is shown with inner shaft 455 passing through the center of the approximately cylindrical scaffold 450. Connectors 460 include loops 460A and loop connectors 460B. Loop connectors 460B connect the loops 460A to the scaffold 450. The inner shaft 455 passes through the loops 460A. The connectors 460 project inwardly from the cylindrical plane of the scaffold 450. Specifically, the loop connectors 460B are flexible so that the angle at which the loop connector 460B projects inward changes (e.g., increases, for example, when the scaffold is expanded from the unexpanded/crimped state). The expanded self-expandable scaffold 450 is shown with one connector 460 towards the distal end of the scaffold and one connector 460 towards the proximal end of the scaffold. The connectors 460 may be disposed on or attached to the distal and/or proximal ends of the scaffold 450. The expandable scaffold may have two or more connectors, preferably in the form of loops. In one embodiment, the expandable scaffold has two connectors, preferably in the form of loops. Each connector 460 has loops 460A through which the inner shaft 450 may pass and a connector 460B, which is attached to the scaffold 450. The connectors 460 are configured such that the inward facing loops position the inner shaft 455 along a longitudinal axis (shown in FIG. 8A) passing approximately through the center of the scaffold 450. The loops of connectors 460, when the scaffold 450 is in its expanded state, align along a longitudinal axis L running approximately through the center of the scaffold. The scaffold 450, inner shaft 455 and loops 460A all share a common longitudinal axis and/or have a concentric axis. As the inner shaft 455 passes through these loops, it positioned along this axis and is thereby approximately centered in the scaffold. The length of the connectors 460 may also define the maximal expansion obtainable by the scaffold. Specifically, for a connector having a circular shape or loop the maximal expansion obtainable by a scaffold with at least two connectors is the length of two connectors and the diameter of the loop. The angle at which connectors project inwardly may vary. In one embodiment, each connector may project inwardly at the same angle. As shown, the loops 460A define a plane this is substantially perpendicular to the longitudinal axis L.

Figure 8B:
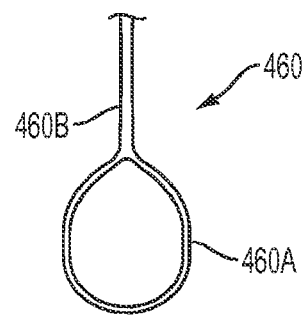
FIG. 8B shows a perspective view of an embodiment of a loop member of a scaffold in accordance with the principles of the invention.

FIG. 8B is a perspective view of a loop of a scaffold in accordance with principles of the invention. Specifically, FIG. 8B shows one connector 460 (which may be used in a scaffold as described above with reference to FIG. 8A) having loop 460A and loop connector 460B. The loop 460A is configured for passing over a catheter. The size and configuration of the loop 460A may vary depending on the use. In one embodiment, the loop 460A may be approximately circular. Loop connector 460B connects the loop 460A to a scaffold. The loop connectors 460B may be may be tapered to reduce stress on the scaffold. The loop connectors 460B are configured to move, restore, flex and/or bend as the scaffold expands because one end is attached to the scaffold and the other end is attached to the shaft by the loop. This may be achieved for example by constructing the loop connectors 460B from a memory shape alloy such as nitinol. Specifically, the loop connectors 460B may be configured so that they project inwardly from the inner surface of the scaffold when the scaffold is fully expanded.

Figure 9A:
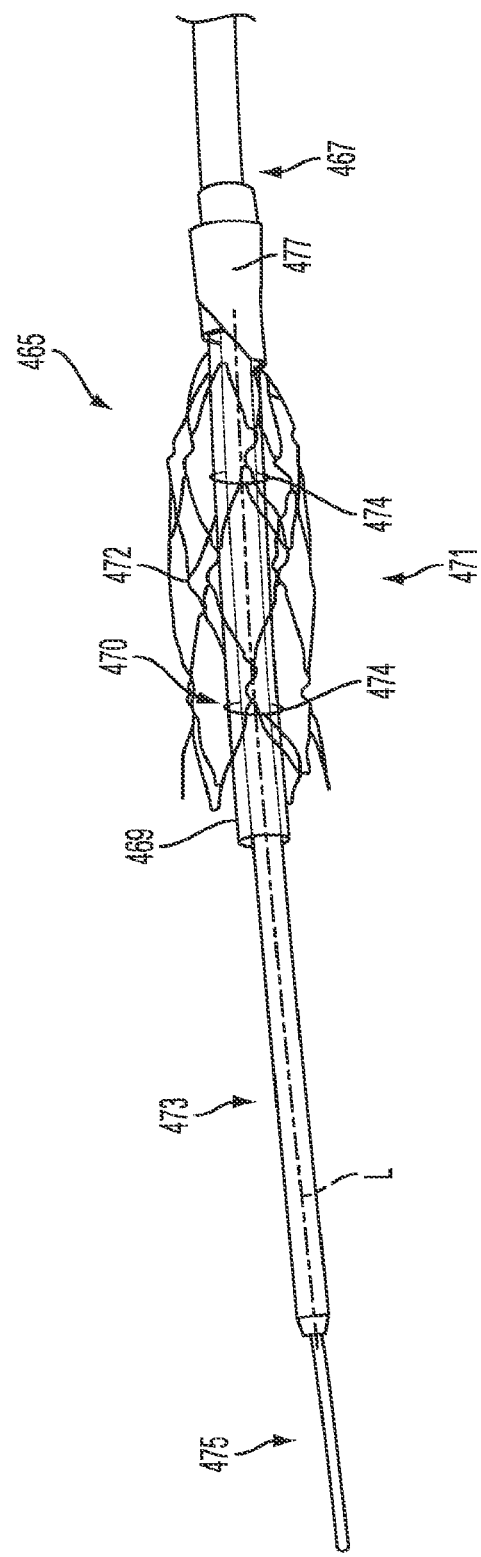
FIG. 9A is a view of a distal end of a catheter apparatus according to one embodiment of the invention.

FIG. 9A is a view of the distal end of a catheter apparatus 465 according to one embodiment of the invention. FIG. 9A shows the distal end of a catheter apparatus with outer shaft (sheath) 467 in a partially retracted position. Catheter apparatus 465 can have any of the features of a catheter apparatus disclosed herein. In particular, catheter apparatus 465 includes expansible scaffold 471 having a proximal and distal end. The scaffold 471 is disposed on the distal end of the inner shaft 469. The proximal end of the scaffold 471 is secured to 469. While the distal end is not attached to 469 as shown in the expanded configuration in FIG. 9A. The expansible scaffold 471 may include a cellular configuration of cells 470. Each cell 470 is approximately hexagonal and has expansible S-shaped (zig-zag) connectors 472 on two opposing sides of the hexagon. In one embodiment, these S-shaped (zig-zag) connectors are approximately parallel to an axis passing through the center of the scaffold from the distal to the proximal end. The scaffold also includes connectors 474 including the type described herein such as inward projecting loops. The loops are configured for allowing the inner shaft 469 to pass through them. The number and configuration of the loops and cells, including the connectors, may vary. The connectors 474 center the shaft 469 in the scaffold 471. As in other embodiments of the invention, the outer shaft 467 is movable relative to the inner shaft. Optional outer shaft tip 477 is configured for passing over the expansible scaffold 471. The catheter apparatus further includes microcatheter 473 which passes through a lumen in inner shaft 469. Microcatheter 473 has a lumen through which guidewire 475 may pass. Similar to the other embodiments of the invention, inner shaft 469, microcatheter 473 and guidewire 475 may telescope independently of each other, in both directions. As shown, for reliable centering of the microcatheter the scaffold 471 and inner shaft 469 share a common longitudinal axis L and are concentric.

Figure 9B:
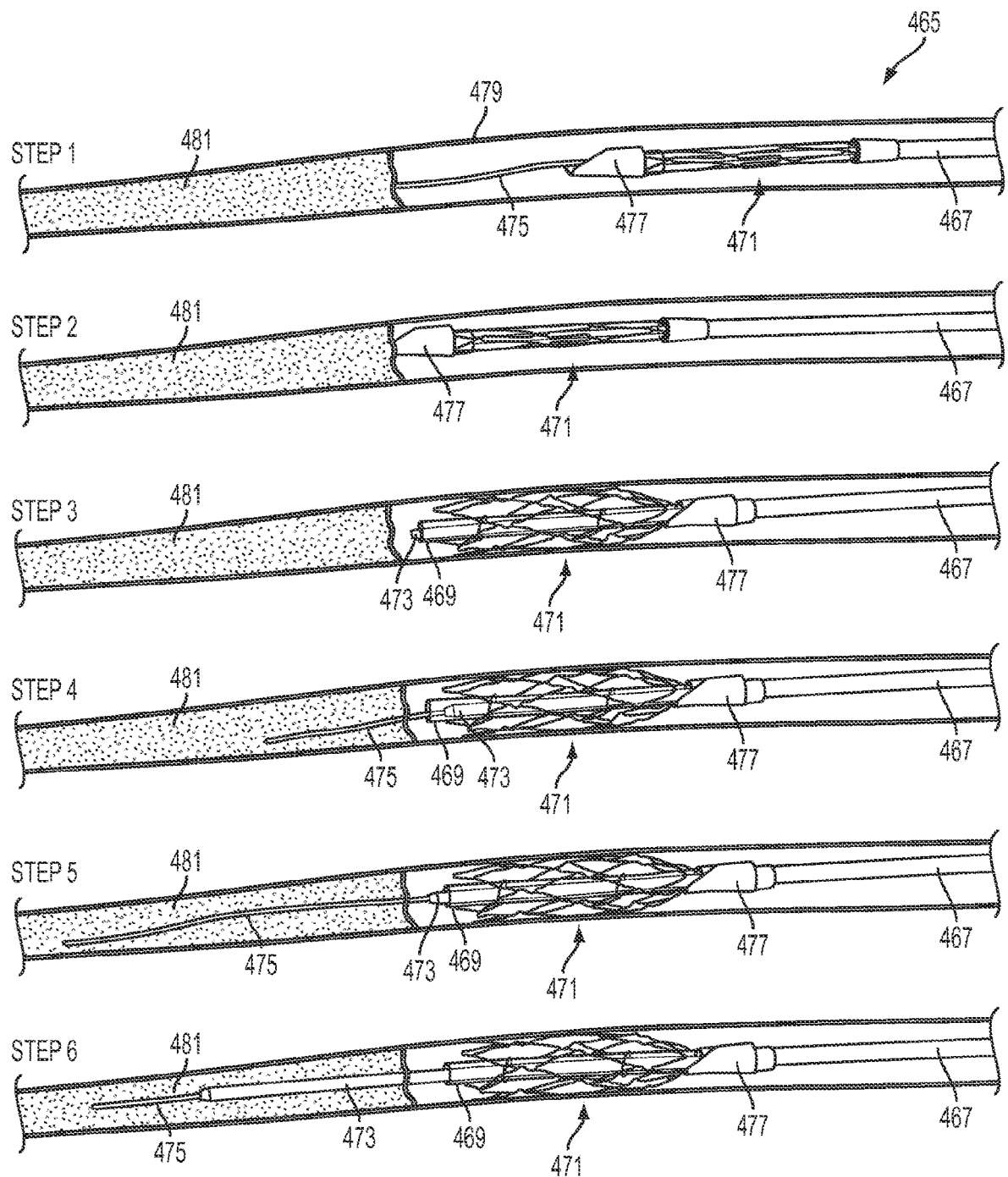
FIG. 9B illustrates an embodiment of the steps during a method of using the catheter apparatus shown in FIG. 9A.

FIG. 9B illustrates an embodiment of the steps during a method using catheter apparatus 465 shown in FIG. 9A the catheter apparatus 465 approaches the CTO tracking along guide wire 475 positioned proximate the CTO but unable to cross. In FIG. 9B, catheter apparatus 465 is shown in six steps inserted into vasculature 479 having occlusion 481. FIG. 9B shows a cut away of the vasculature 479 and chronic total occlusion 481 with catheter apparatus 465. Steps 1 and 2 of FIG. 9B show the outer shaft or sheath 467 covering the expansible scaffold 471 and hold it in an unexpanded position. The inner shaft 469 is threaded through the loop 460A. The first step of the operation of the catheter apparatus 465 is insertion of the catheter apparatus 465 into vasculature 479 close to occlusion 481. As shown in Step 1, the catheter apparatus 465 is advanced with the scaffold 471 in its refracted or compressed position. In the retracted position, scaffold 471 is covered by outer shaft 467 and outer shaft tip 477. Guidewire 475 has been advanced into contact with occlusion 481 as shown in step 1 for the system to track over. The catheter apparatus 465 is advanced over guidewire 475 towards the CTO 481 as shown in step 1 with the catheter apparatus approaching the CTO. Once the catheter apparatus has been engaged or contact with the CTO or in close proximity to the CTO, as shown in step 2, outer shaft tip 477 is in close proximity to the occlusion 481, in particular, contacts the leading edge of the CTO. Expansible scaffold 471 is still in its compressed or non-expanded position. The outer shaft 467 is then retracted or withdrawn such that the expansible scaffold 471 assumes its expanded state (as shown in step 3). Expansible scaffold 471 has loops through which the inner shaft 469 is positioned and microcatheter 473 is positioned in the inner shaft. All are centered in the scaffold when expanded (as shown in step 3). Thus, microcatheter 473 is substantially centered in vasculature 479. Step 1 shows catheter apparatus 465 advanced into vasculature 479 with guidewire 475 extended but without sufficient support to cross the CTO/lesion. Step 2 shows the catheter apparatus 465 advanced by tracking over the guidewire 475 so that outer shaft tip is pushed against the (leading) edge of the CTO. Steps 4 and 5 of FIG. 9B show further advancement of the guidewire 475 into contact with and through the occlusion 481. Alternatively, the microcatheter 473 may also be advanced into contact and through the occlusion 481. Step 6 shows catheter apparatus 465 with microcatheter 473 and guidewire 475 advanced through the occlusion 481. The microcatheter 473 adds support to the guidewire 475 as it passes through the CTO. The guidewire and the microcatheter can be advanced alternatively back and forth.

Figure 9C:
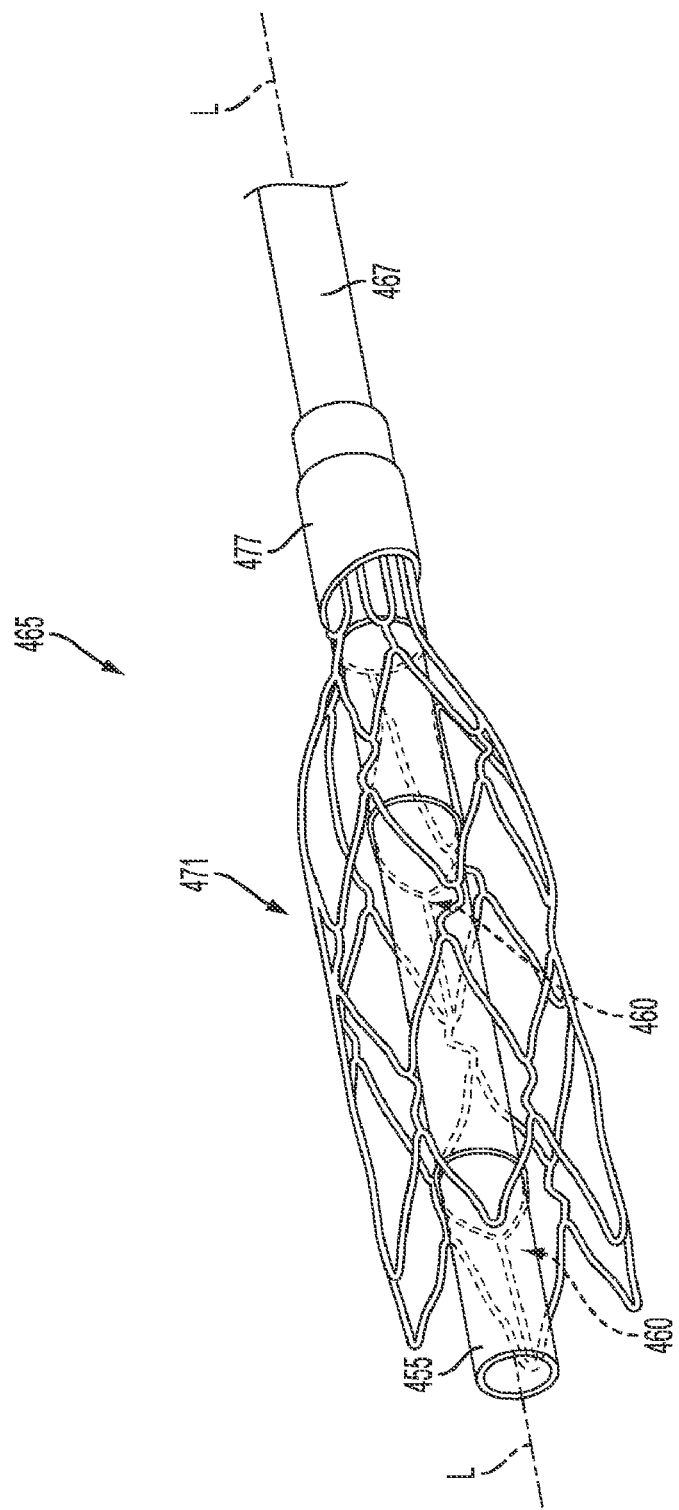
FIG. 9C is a close-up view of a distal end of a catheter apparatus shown in FIG. 9A according to an embodiment of the invention.

FIG. 9C is a close-up view of the distal end of catheter apparatus 465 shown in FIG. 9A with outer shaft (sheath) 467 in a partially retracted position. As discussed above with reference to FIG. 9A, catheter apparatus 465 includes expansible scaffold 471 having a proximal end disposed on the outer shaft 467, while the inner shaft 469 passes through the scaffold 471. The expansible scaffold 471 may be configured so that it has a central longitudinal axis L along which the inner shaft 455 passes. The expansible scaffold 471 includes cells 470. Each cell is approximately hexagonal and has expansible S-shaped (zig-zag) connectors 472 on two opposing sides of the hexagon. The scaffold also includes inward projecting loops 460A, which are configured for passing the inner shaft 455 therethrough. The loops 460A may project inward so that the loops are positioned along the central longitudinal axis L of the expansible scaffold 471. The optional outer shaft tip 477, which may be tapered, is also shown. In certain embodiments, the outer shaft tip 477 may be used to maintain the position of the expansible scaffold 471. The taper of the outer shaft tip 477 may assist in allowing the outer shaft 467 to pass over the scaffold 471, and may also be beneficial in navigating the catheter into inner branches of the vasculature.

Figure 9D:
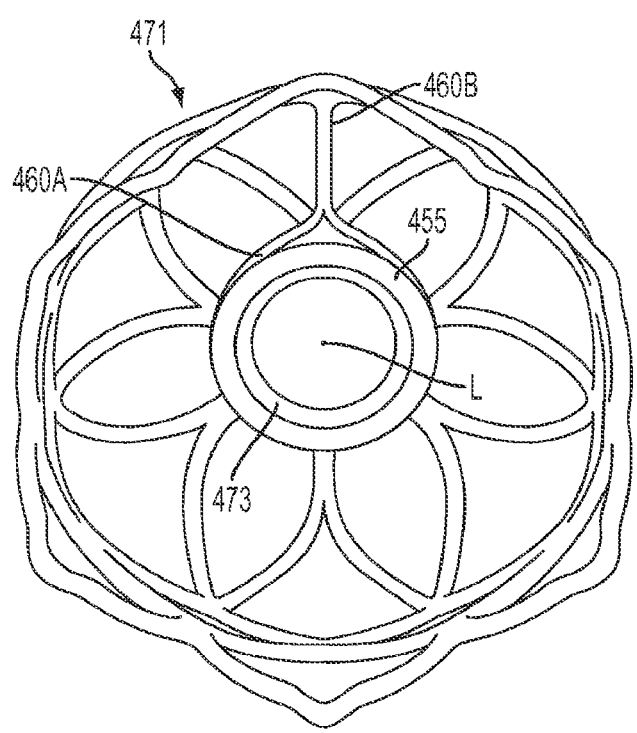
FIG. 9D is a distal end view of the catheter apparatus shown in FIG. 9C according to an embodiment of the invention.

FIG. 9D is a distal end view of the distal end catheter apparatus 465 shown in FIGS. 9A and 9B. Specifically, as shown in FIG. 9B, the inner shaft 469 is shown positioned along the central longitudinal axis of expansible scaffold 471 via inward projection loop 474. This configuration allows the device to the centered in a vasculature while in operation and, more particularly, to center the microcatheter. Thus, the guidewire as shown in FIG. 9B may pass through the center of the CTO. Microcatheter 473 is shown passing through the inner shaft 469. Guidewire 475 (not shown) may pass through microcatheter 473.

Figure 10A:
FIG. 10A is a side view of an alternate embodiment of a scaffold according to the principles of the invention.
Figure 10B:
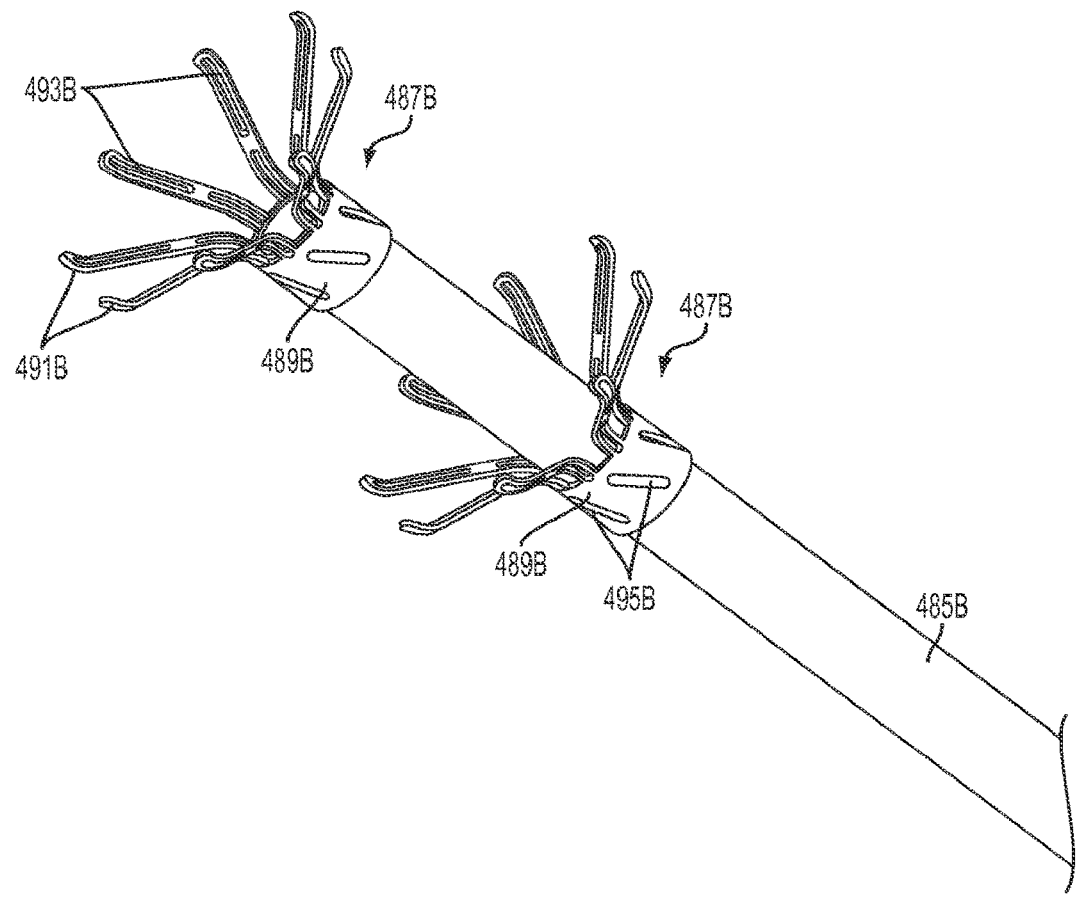
FIG. 10B is perspective view of the scaffold of FIG. 10A in accordance with principles of the invention.

FIGS. 10A to 10C illustrate alternate embodiments of scaffolds useful in the catheters apparatus of the invention. For illustration purposes only the scaffold are shown on the inner shaft. When used in a catheter apparatus of the invention, the apparatus may include the inner shaft, outer shaft, scaffold, and other features as described herein. In this embodiment, the scaffold is configured without outwardly extending extensions with free ends. As shown, these extensions may be described as forming the shape of a flower with the inner shaft passing through the center and the petals of the flower (i.e., the arms of the scaffold) radiating out from inner shaft when the scaffold is expanded. More specifically, this "flower" scaffold includes a center band and arms that are attached to the center band at one end and the other end is flexible. The center band is disposed on the inner shaft. The arms expand radially out from the center band to a predetermined diameter. This predetermined diameter may be based on flexibility of the material used to manufacture the arms. The arms of this embodiment may aid with the centering of the inner shaft, microcatheter, and/or guidewire.

FIG. 10A shows inner shaft 485A which has one or more expansible scaffolds 487A disposed towards the distal end of the shaft. The inner shaft 485A has a lumen for passing a microcatheter. The scaffolds 487A are shown in their expanded position. One of the one or more scaffolds 487A may be attached to the distal end of the inner shaft 485A. While one or two scaffolds 487A may be used in certain embodiments of the invention, the number and configuration of the scaffold varies depending on the use. Thus, in certain embodiments, one or more, two or more or three or more of scaffolds 487A may be used. Each of the one or more scaffolds 487A includes a center band 489A and arms 491A. The arms 491A may be thin strips of material which may be rounded towards their distal end. The number of arms in each of the scaffolds may vary depending on use. For example, the scaffold may contain three, four, six or eight arms or other combinations. More arms provide more coverage and potentially better centering. The scaffold size and flexibility may decrease as the number of arms increase. Arms 491A may be disposed on, attached to or integral with center band 489A. Center band 489A is disposed on inner shaft 485A.

FIG. 10B is a perspective view of inner shaft 485B having self-expansible scaffolds 487B. Like in FIG. 10A, the scaffolds are shown in their expanded position. Each of the arms 491B of the scaffold 487B may have openings 493B towards their distal end. The openings 493B may be approximately circular, rectangular or oval. The configuration of openings 493B may vary depending on the use. When in a vasculature, the arms 491B may contact the surface of the vasculature when scaffold 487B is expanded. When expanded, the arms may curve such that they contact the vasculature towards their distal end. The arms 491B may be curved to maximize the contact area between the distal end of the arms and the surface of the vasculature. For example, the distal end of the arms 491B may curve such that the distal tip of the arms 491B is approximately parallel to the inner shaft 485B when the scaffold is fully expanded. The openings in the arms help to increase flexibility while covering more surface area. The surface area is important since it helps to spread the force of the arms on the vessel wall. Each center band 489B may have openings 495B around its circumference. The openings 495B may be approximately rectangular although the configuration and number of the openings 495B may vary depending on the use. The openings in the center band of the scaffold may provide for additional reinforcement to the scaffold and inner shaft bond. The center band may be attached to the inner shaft via a biocompatible adhesive. The adhesive is meant to fill the gap between the center band and inner shaft. The adhesive is also meant to partially fill the openings on the center band, creating an additional mechanical lock for this bond.

FIG. 10C is an unwrapped view of scaffold 487C, which is another embodiment a "flower" scaffold. As shown in FIG. 10C, the openings 495C in center band 489C may be oval. The shape and number of the openings may vary depending on their use. With reference to FIG. 10C, each of the arms 491C of the scaffold 487C has distal opening 493C at their end. Furthermore, each of the arms may have further openings 497C. The openings in the arms may help to increase flexibility of the arms while covering more surface area. This surface area helps to spread the force of the arms on the vessel wall. As shown in FIG. 10C, the arms 491C may be integrally formed with center band 489C. Thus, the scaffold may be made from a single sheet of self-expansible material such as, e.g., a foil. In alternate embodiments, the scaffold may be assembled by mounting the arms 491C onto center band 489C.

Nitinol and/or stainless steel may be incorporated into scaffolds 487A, 487B, and 487C. Nitinol is an illustrative example of a shape memory alloy. Other shape memory alloys or other similar substances may be used.

A scaffold configured as shown in FIG. 10A-C has certain benefits. First, it may be more flexible since it not one continuous piece, but two or more pieces. Second, the arms may be added or removed and spaced optimally to help provide optimal centering. Furthermore, due the configuration of the scaffold, the inner shaft remains is positioned approximately in the center of self-expandable scaffold structure. Furthermore, inner shaft also remains approximately centered vessel in the chronic total occlusion. In addition, where one or two scaffolds are used, the scaffold of the catheter apparatus can be compact providing for a low profile. This can make delivery and use easier.

Like the other scaffolds of the invention, the "flower" scaffold provides self-expanding, anchoring support and may be non-occlusive, allowing blood flow to collateral and branch vessels. Optimally, the scaffold has a broad working range (i.e., one size fits all). The scaffold may also be tailored for the specific intended uses. The structure may be used alone, and/or in combination with other structures and/or features, to position the catheter apparatus in the artery and to position the one or more microcatheters substantially centered in the middle of the scaffold/artery. The scaffold may be atraumatic to the vessel wall thereby requiring minimal hoop strength to maintain position. The scaffold is configured to re-sheath to facilitate withdrawal and can be employed multiple times.

Figure 11A:
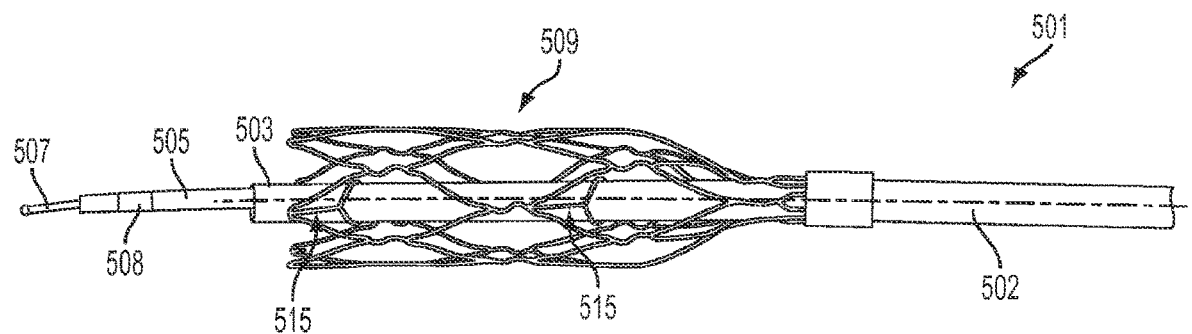
FIG. 11A is a view of a distal end of a catheter apparatus showing another embodiment of a scaffold in accordance with principles of the invention.
Figure 11B:
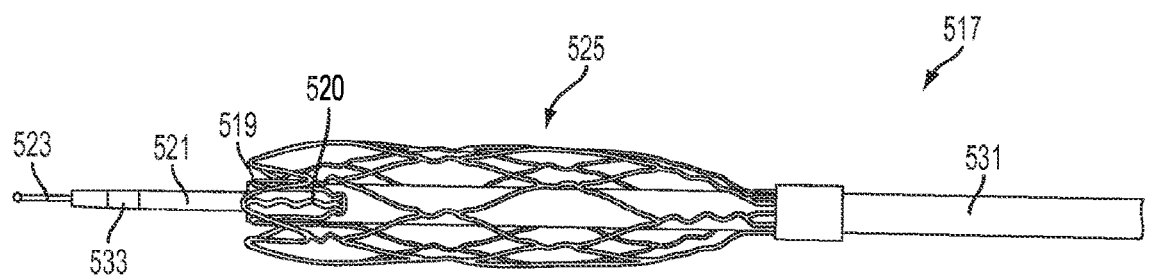
FIG. 11B is a view of a distal end of a catheter apparatus showing yet another embodiment of a scaffold in accordance with principles of the invention.
Figure 11C:
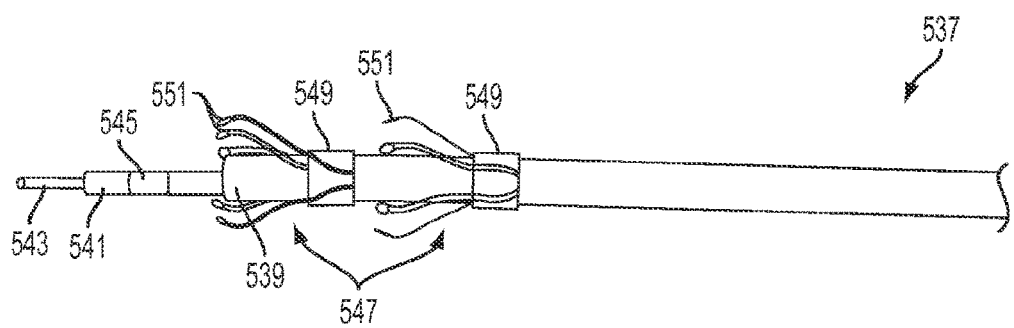
FIG. 11C is a view of a distal end of a catheter apparatus showing of an alternate embodiment of a scaffold in accordance with principles of the invention.

FIGS. 11A to 11C are views of the distal end of catheter systems in accordance with embodiments of the invention with different exemplary suitable self-expandable scaffold configurations. FIG. 11A is a view of a distal end of a catheter apparatus having an open-ended scaffold in accordance with one embodiment of the invention. This scaffold configuration is similar to the configuration shown in FIG. 9A and is characterized by a scaffold which has inward facing loops through which the inner shaft passes. The distal end of the scaffold is attached to the inner shaft. FIG. 11B is a view of a distal end of a catheter apparatus having a scaffold as described above in FIGS. 2A, 2B, and 7. This "football" scaffold is characterized by being approximately cylindrical in shape and with the ends curving towards the inner shaft. The distal end of the scaffold is disposed towards the distal end of the inner shaft without being attached. The proximal end of the scaffold is attached to the distal end of the inner shaft. FIG. 11C is a view of a distal end of a catheter apparatus having a scaffold similar to that described in FIGS. 10A to 10C in accordance with principles of the invention.

In particular, FIG. 11A shows catheter apparatus 501 having inner shaft 503, microcatheter 505 and expansible scaffold 509. The catheter apparatus may further have a retractable sheath, which may slide over the inner shaft 503 and expansible scaffold 509. The inner shaft 503 has one or more lumens. The microcatheter 505 passes through one of the one or more lumens in the inner shaft. The microcatheter 505 has a lumen configured for passing guidewire 507. The microcatheter 505 may have marker band 508 towards its distal end. The expansible scaffold 509 has a cellular configuration. The scaffold further includes one or more inward facing connectors 515 through which the inner shaft 503 passes. The inward facing loops project inwardly from the cylindrical plane of the scaffold. In one embodiment, the scaffold has two inward facing loops 515. In that embodiment, one of the inward facing loops 515 may be positioned towards the proximal end of the scaffold, while the other may be positioned towards the distal end. The scaffold is configured so that upon expansion of the scaffold, the inner shaft 503 and therefore also microcatheter 505 and guidewire 507 are centered in the scaffold via inward facing loops. Specifically, this configuration is achievable because the inward facing loops (when the scaffold is expanded) align to create and/or maintain a common a longitudinal axis through the center of the scaffold, inner shaft, and microcatheter. The inner shaft 503 passes through the inward facing loops and therefore along the longitudinal axis of the device when the scaffold is in its expanded state. Thereby the inner shaft is centered in the scaffold. Since the scaffold when in use is centered in a chronic occlusion, after expansion and in-situ, the inner shaft 503 and therefore also microcatheter 505 and guidewire 507 are also centered in the chronic occlusion. They share a common longitudinal axis. The inward facing connectors 515 are connected to the scaffold via the loop support and loop configuration described herein. In one embodiment, the connector is approximately linear when the scaffold is in its expanded state.

FIG. 11B shows catheter apparatus 517 having inner shaft 519 with scaffold 525 disposed towards the distal end. Microcatheter 521 passes through a lumen in inner shaft 519. Microcatheter 521 is also configured for passing guidewire 523. The scaffold 525 has a distal end and a proximal end. The proximal end of scaffold 525 is disposed on or attached to towards the distal end of inner shaft 519. The distal end of scaffold 525 is disposed on or attached to the distal end of inner shaft 519, preferably slidably disposed or attached. The distal end of the scaffold 525 may be slidably disposed or attached to the inner shaft 519 by, for example, an inverted portion 520 of the scaffold 525. The expansible scaffold 525 includes a cellular configuration. The microcatheter may have a marker band 533 towards the distal end. Optionally, catheter apparatus 517 also has a retractable sheath 531 which may slide over the inner shaft 519 and expansible scaffold 525. The scaffold is configured so that upon expansion that upon expansion of the scaffold, the inner shaft 519 and therefore also microcatheter 521 and guidewire 523 are centered in the scaffold. Since scaffold when in use is centered in a chronic occlusion, inner shaft 519 and therefore also microcatheter 521 and guidewire 523 are also centered in the chronic occlusion.

FIG. 11C shows catheter apparatus 537 having inner shaft 539, one or more expansible scaffolds 547 and microcatheter 541. The inner shaft 539 has one or more lumens. The microcatheter 541 passes through a lumen in the inner shaft 539. The microcatheter 541 is configured for passing a guidewire 543. Optionally, the microcatheter 541 includes a marker band 545. The one or more expansible scaffolds are of the type having projections, fingers, tabs or members as shown above in FIG. 10A to 10C. In one embodiment, they may be a "flower scaffold." Each of the one or more expansible scaffolds 547 have a center band 549 which is disposed on or attached to the inner shaft 539. Attached to each center band 549 are arms 551, which radiate out when the scaffold expands. The arms 551 may be wire loop with one or more openings. In another embodiment, the center band 549 and arms 551 are made from a sheet of self-expanding material such as nitinol. When the one or more scaffolds expand in an occlusion, the inner shaft 539 (and, therefore, also the microcatheter 541 and guidewire 543) are centered in the occlusion.

Figure 12A:
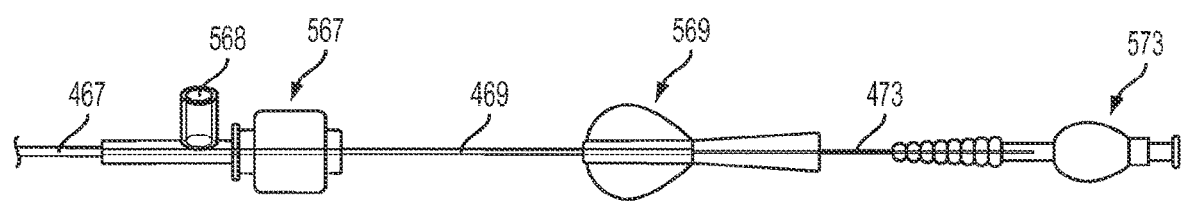
FIG. 12A shows a proximal end of a catheter apparatus when a scaffold is disposed within a sheath according to one embodiment of the invention.

FIG. 12A shows a proximal end of a catheter system in accordance with another embodiment of the invention. The inner shaft 469 may be disposed within the outer shaft 467 through an opening in the outer shaft hub 567. Microcatheter 473 can be disposed within the inner shaft 469 through the inner shaft hub 569. The microcatheter hub 571 may include an opening through which a guidewire (not shown) may inserted. Any of the outer shaft 467, inner shaft 469, and microcatheter 473 may be movable independently of the others. For example, during use of the catheter, an operator of the catheter may grip one or more of hubs 567, 569, and 571 in order to move one or more of the hubs relative to another. This results in a relative sliding of the outer shaft 467, inner shaft 469, or microcatheter 473 with respect to the others. The outer shaft 467 also may include a port 568 near or integral with the outer shaft hub 567. A lumen of the port 568 may be in fluid communication with a longitudinal lumen of the outer catheter.

Figure 12B:
FIG. 12B shows a distal end of a catheter apparatus of FIG. 12A with the scaffold within the sheath according to one embodiment of the invention.

FIG. 12B shows a distal end of the catheter system according to an embodiment. Specifically, FIG. 12B shows the relative positions of the outer shaft 467 and inner shaft 469 when the proximal end of the catheter apparatus is in the position shown in FIG. 12A. For example, when the outer shaft hub 567 and the inner shaft hub 569 are spaced apart in the manner shown in FIG. 12A, the distal end of the inner shaft 469 is disposed within the distal end of the outer shaft 467. In this way, the scaffold 473 (not shown in FIG. 12B) may be contained in a non-expanded state within the outer shaft 467.

Figure 12C:
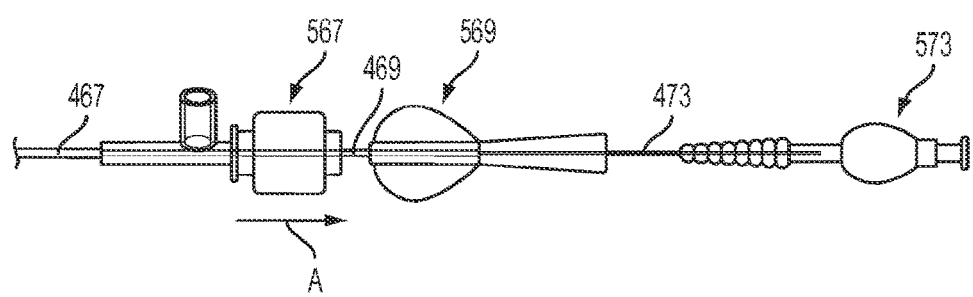
FIG. 12C shows a proximal end of a catheter apparatus of FIG. 12A when the scaffold is uncovered by the sheath according to one embodiment of the invention.

FIG. 12C shows the proximal end of the catheter after the outer shaft hub 567 and the inner shaft hub 569 are moved relative to one another. For example, the outer shaft hub 567 may be moved in the proximal direction (i.e., away from the distal end of the catheter), as indicated by arrow A in FIG. 12C. However, it is also possible to move the inner catheter hub 569 in the distal direction (i.e., the opposite of arrow A) while holding the outer shaft hub 567 in place. Though not shown, the microcatheter hub 571 may be moved relative to the outer and inner shaft hubs 567, 569 in a similar fashion.

Figure 12D:
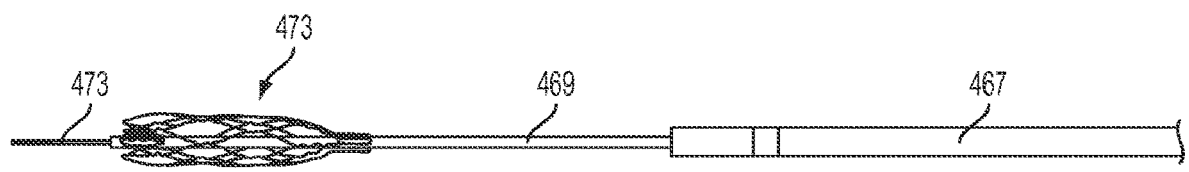
FIG. 12D shows a distal end of a catheter apparatus of FIG. 12A with the scaffold uncovered by the sheath according to one embodiment of the invention.

FIG. 12D shows the distal end of the catheter when the proximal end is arranged as shown in FIG. 12C. As shown in FIG. 12D, by shortening the distance between outer shaft hub 567 and inner shaft hub 569 (see FIG. 12C), the distal end of inner shaft 469 and the scaffold 473 have emerged from the distal end of the outer shaft 467, and the scaffold 473 has therefore expanded to an expanded state.

Figure 13A:
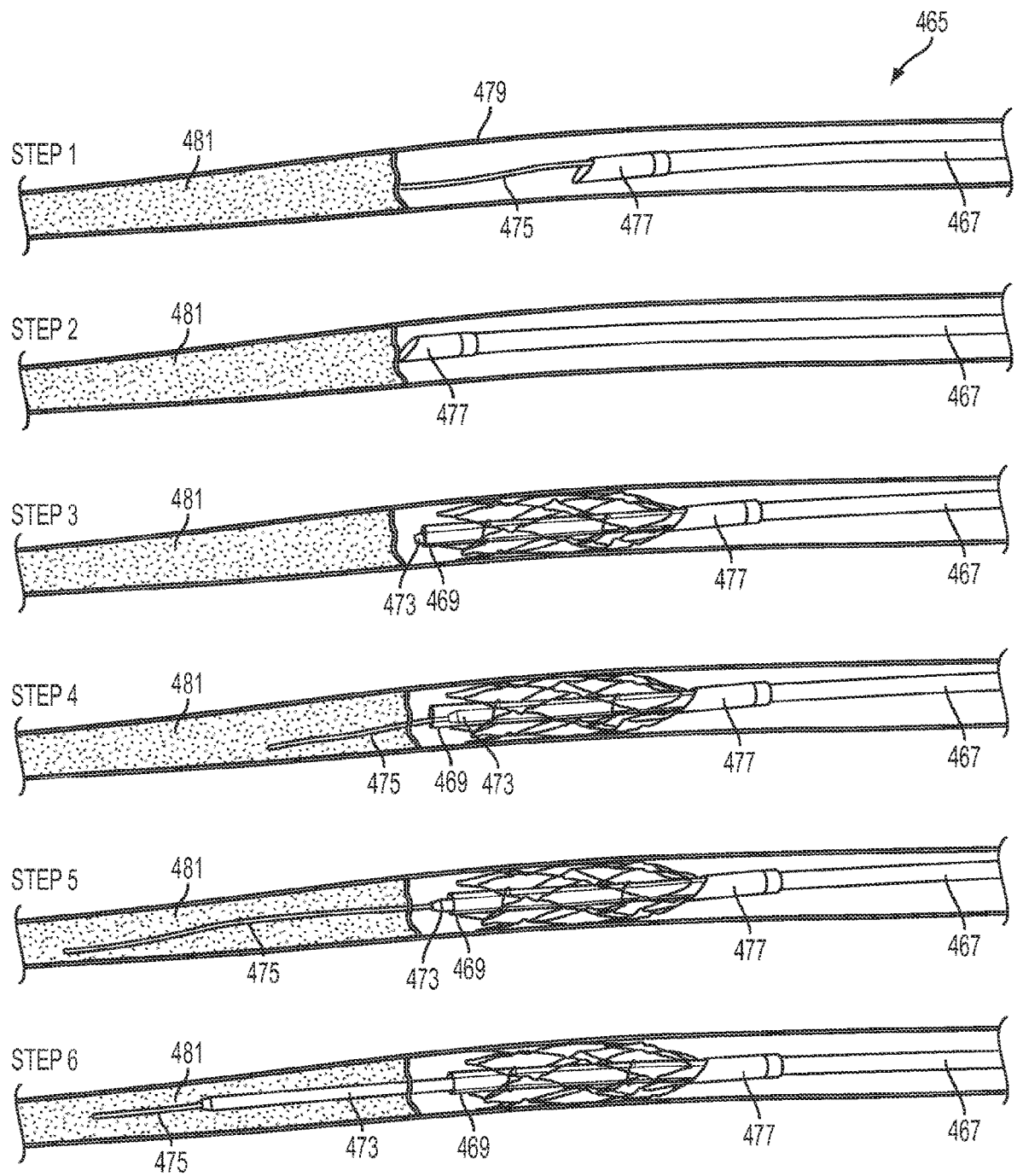
FIG. 13A illustrates an embodiment of steps during a method of using the catheter apparatus shown in FIG. 12A according to one embodiment of the invention.
Figure 13B:
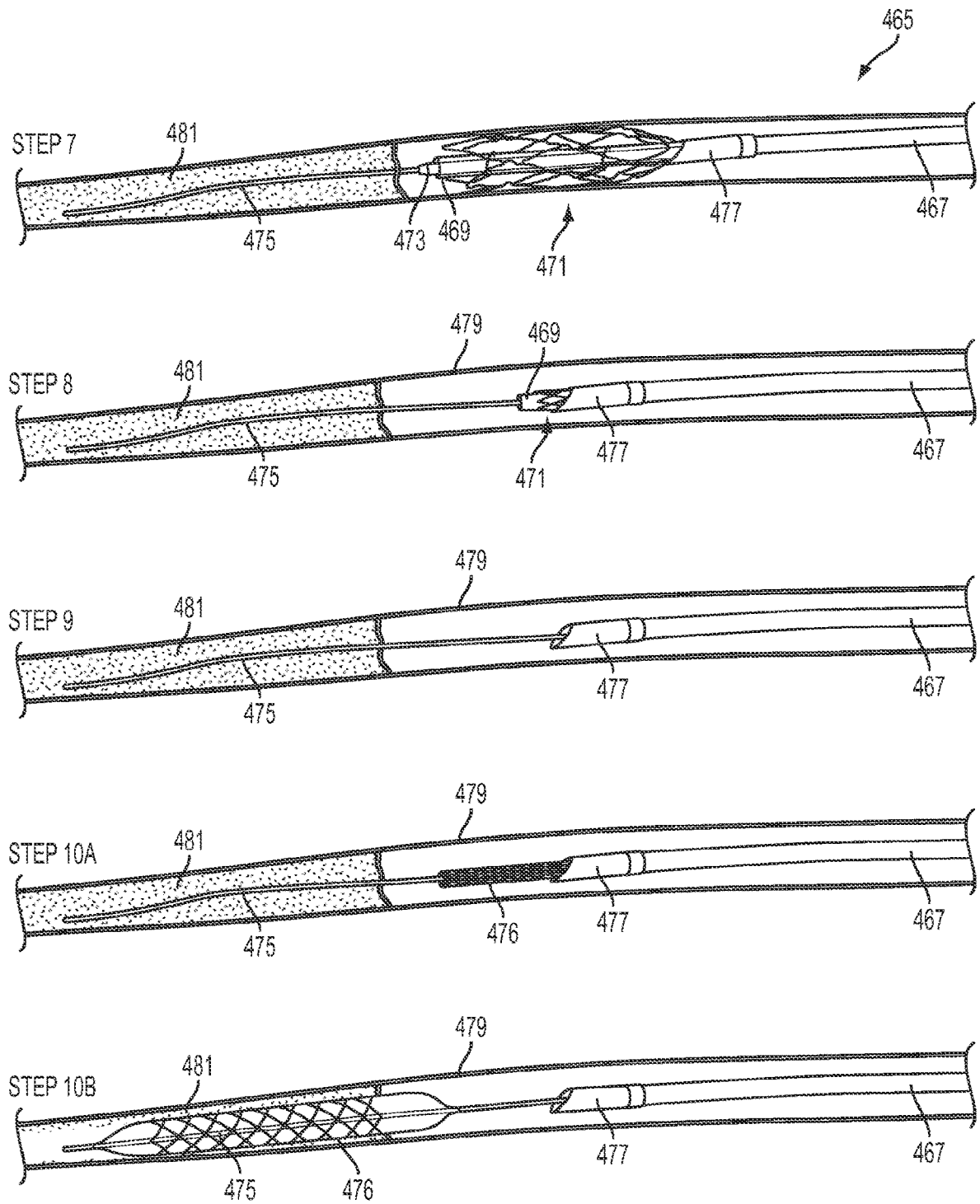
FIG. 13B illustrates an embodiment of additional steps during a method of using the catheter apparatus shown in FIG. 12A according to one embodiment of the invention.

With reference to FIGS. 13A-13B, a method is described using the catheter apparatus shown, for example, in FIG. 12A. Although illustrated with an embodiment of the catheter apparatus as shown, the other catheter embodiments and various combinations thereof described and incorporated herein may also be used in accordance with the methods described herein.

FIGS. 13A-13B illustrate an embodiment of the steps during a method using catheter apparatus 465 shown in FIG. 13A. The catheter apparatus 465 approaches the CTO tracking along guide wire 475 positioned in proximity of the CTO but unable to cross. In FIG. 13A, catheter apparatus 465 is shown in six steps inserted into vasculature 479 having occlusion 481. FIG. 13A shows a cut away of the vasculature 479 and chronic total occlusion 481 with catheter apparatus 465. Steps 1 and 2 of FIG. 13A show the outer shaft or sheath 467 covering the expansible scaffold 471 and hold it in an unexpanded position. The inner shaft 469 is threaded through the loop 460A. The first step of the operation of the catheter apparatus 465 may be insertion of the catheter apparatus 465 into vasculature 479 close to occlusion 481. As shown in Step 1, the catheter apparatus 465 can be advanced with the scaffold 471 in its retracted or compressed position. In the retracted position, scaffold 471 can be covered by outer shaft 467 and outer shaft tip 477. Guidewire 475 has been advanced into contact with occlusion 481 as shown in step 1 for the system to track over. The catheter apparatus 465 may be advanced over guidewire 475 towards the CTO 481 as shown in step 1 with the catheter apparatus approaching the CTO. Once the catheter apparatus has been engaged or contact with the CTO or in close proximity to the CTO, as shown in step 2, outer shaft tip 477 may be in close proximity to the occlusion 481, in particular, contacts the leading edge of the CTO. Expansible scaffold 471 is still in its compressed or non-expanded position. The outer shaft 467 can then be retracted or withdrawn by, for example, decreasing a distance between the outer shaft hub 567 and inner shaft hub 569, as shown in FIG. 12C. The expansible scaffold 471 assumes its expanded state (as shown in step 3). Expansible scaffold 471 has loops through which the inner shaft 469 may be positioned and microcatheter 473 is positioned in the inner shaft. All are centered in the scaffold when expanded (as shown in step 3). Thus, microcatheter 473 can be substantially centered in vasculature 479. Step 1 shows catheter apparatus 465 advanced into vasculature 479 with guidewire 475 extended but without sufficient support to cross the CTO/lesion. Step 2 shows the catheter apparatus 465 advanced by tracking over the guidewire 475 so that outer shaft tip may be pushed against the (leading) edge of the CTO. Steps 4 and 5 of FIG. 13A show further advancement of the guidewire 475 into contact with and through the occlusion 481. Alternatively, the microcatheter 473 may also be advanced into contact and through the occlusion 481. Step 6 shows catheter apparatus 465 with microcatheter 473 and guidewire 475 advanced through the occlusion 481. The microcatheter 473 may add support to the guidewire 475 as it passes through the CTO. The guidewire and the microcatheter can be advanced alternatively back and forth to penetrate through the CTO. Although Steps 7-10B in FIG. 13B show the guidewire 475 penetrating through a portion of the occlusion (CTO) 481, it is understood that the guidewire may alternatively be advanced through the entirety of the occlusion 481.

In FIG. 13B, steps are shown of removal of the inner shaft 469 and scaffold 471. The microcatheter 473 may be withdrawn as it is independent from the inner and outer shaft. The result of withdrawing the microcatheter is shown in Step 8 of FIG. 13B, where only the guidewire is disposed through the CTO. Next, the scaffold 471 may be returned to its non-expanded state by advancing the outer shaft 467 in the distal direction until the scaffold is contained with the outer shaft 467, or at least until the scaffold 471 is not expanded. Alternatively, as shown in step 8, the inner catheter 469 may be moved proximally so that the scaffold 471 is received within the outer shaft 467. It is understood from the above discussion that the relative movement of the inner and outer shafts 467 and 469 may be achieved by the relative movement of the proximal ends of these shafts. The hubs 567, 569 of FIG. 12C, for example, may be moved relative to each other to achieve Step 8, for example. As shown in Step 9 of FIG. 13B, the inner catheter 469 and scaffold 471 may be completely removed from the vasculature. If removed completely from the outer shaft 467 via a proximal opening of the outer shaft 467, the outer shaft 467 may remain positioned near a target location within the vasculature. Accordingly, an angioplasty balloon, stent, catheter, scope, imaging or treatment device/material, or additional interventional instrument or medical device (shown in various embodiments as 476 in Steps 10A and 10B of FIG. 13B) may then be placed in the vasculature, as shown in Step 10, using the outer shaft 467 as a guide and as protection for the patient's tissue. The guidewire 475 may also assist in guiding the additional instrument 476, as the guidewire 475 may be left penetrating the occlusion 481 even after removal of the inner catheter 469, as shown in Steps 8-10 of FIG. 13B.

Figure 14:
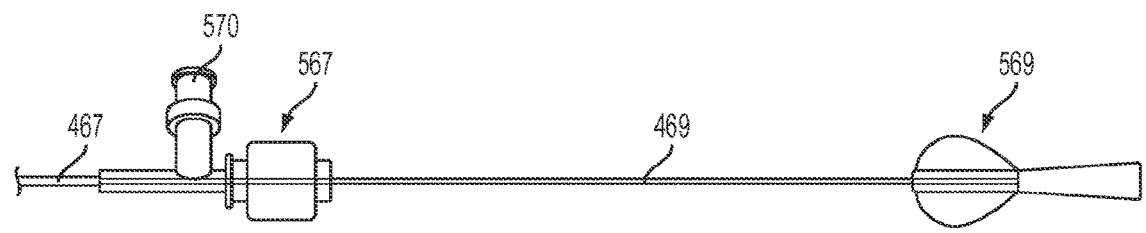
FIG. 14 shows a proximal end of a catheter apparatus according to one embodiment of the invention.

FIG. 14 shows another embodiment of the proximal end of the catheter.

Figure 15A:
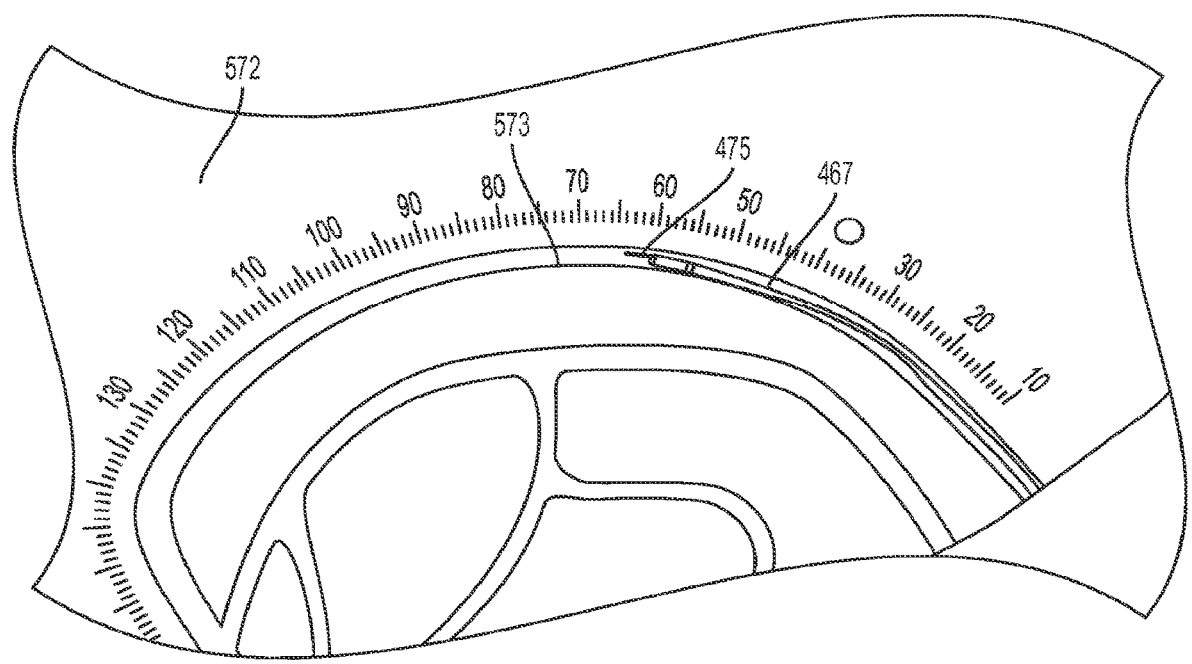
FIG. 15A-15E illustrates an embodiment of the steps during a method of using the catheter apparatus shown in FIG. 12A.
Figure 15B:
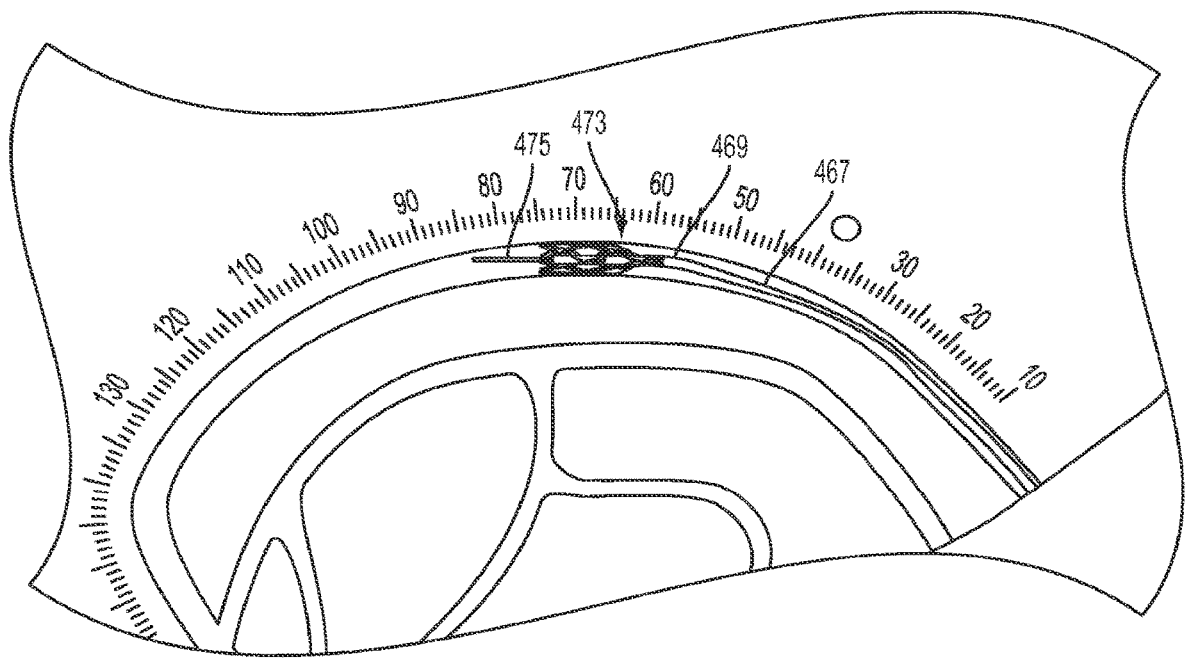
Figure 15C:
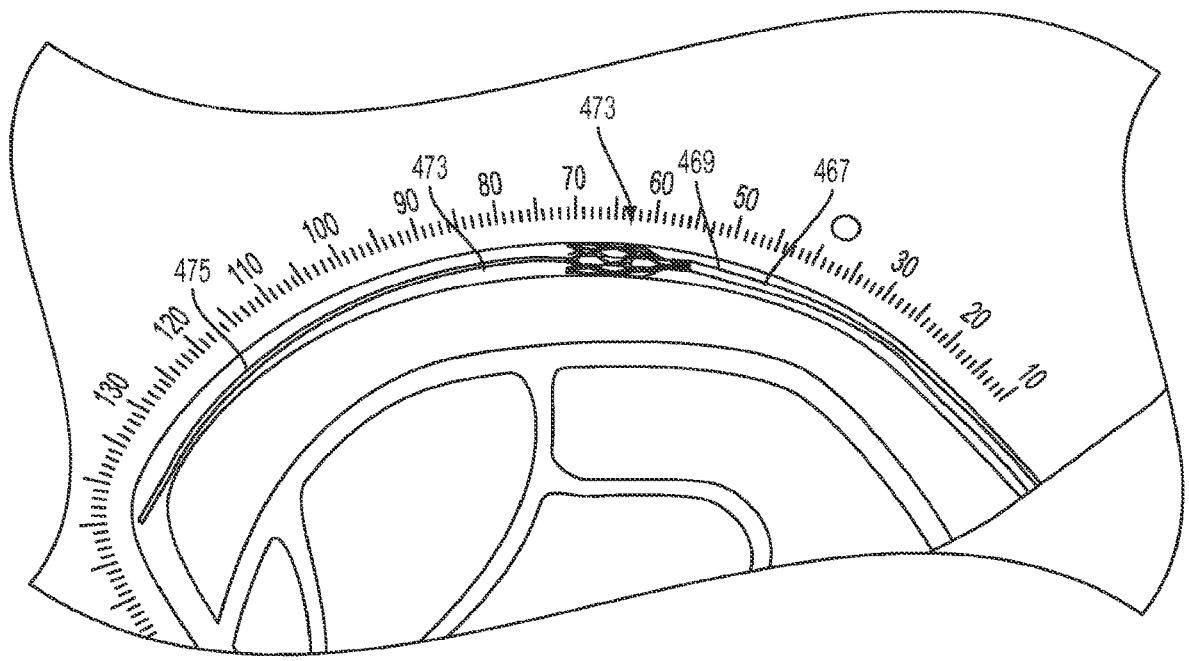

FIGS. 15A-15E shows an example of a catheter according to an embodiment of the invention being used in accordance with an embodiment of the method shown in FIGS. 13A-13B. This example is performed in a model 572 with channels 575 that represent vasculature of a patient. As shown in FIG. 15A, the outer shaft 467 is inserted into the vasculature and the inner shaft has not yet been deployed. A guidewire 475 may be used to insert the outer shaft 467 to the position shown. In FIG. 15B, the inner shaft 469 and scaffold 473 have been deployed from the outer shaft 467. Additionally, the guidewire 475 extends out from the distal end of the inner shaft 469. In FIG. 15C, a microcatheter 473 and the guidewire 475 have both been further into the vasculature in order, for example, to advance through an CTO (not shown).

Figure 15D:
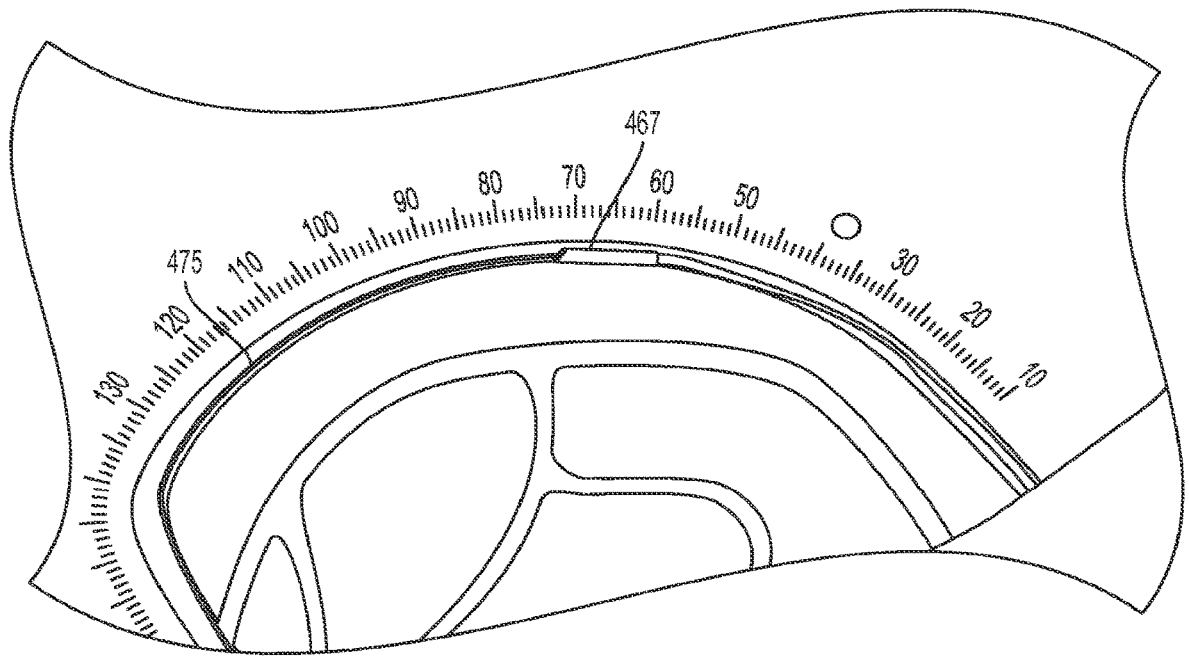
Figure 15E:
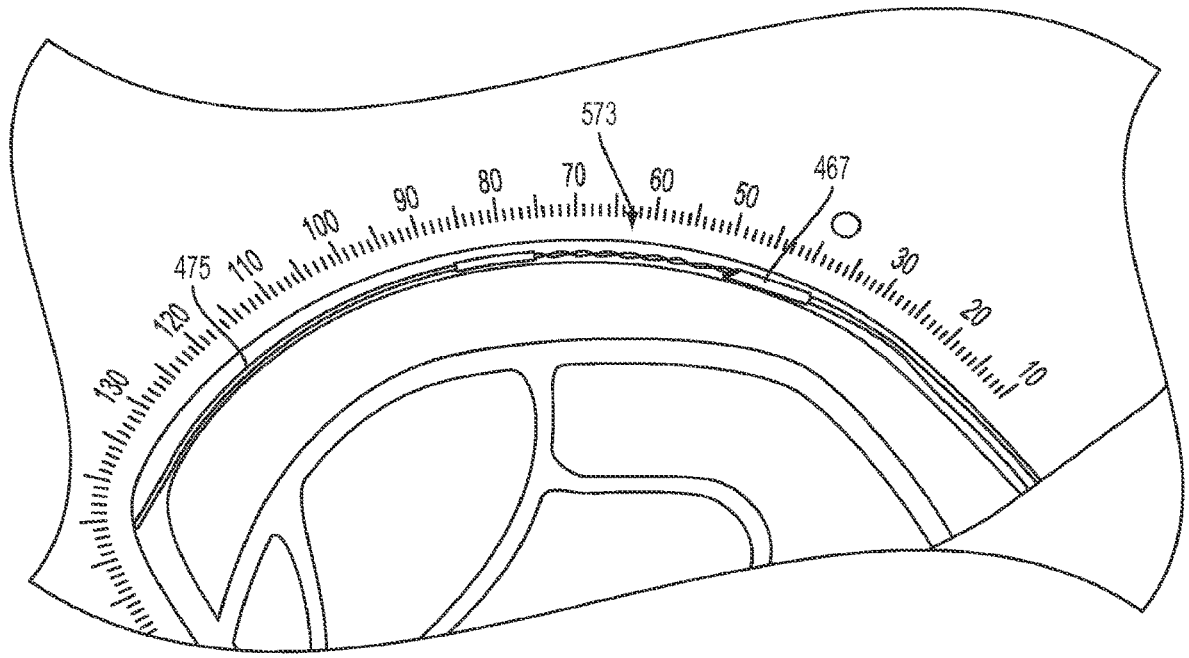

After using the microcatheter 473 in FIG. 15C for its intended purpose, the microcatheter 473 and inner shaft may optionally be withdrawn from the vasculature through the outer shaft 467. FIG. 15D shows an example where the inner shaft 469 and scaffold 473 have been retracted through the outer shaft 467. In some embodiments, the microcatheter 473 and inner shaft 469 are completely removed from the outer shaft 467 through a proximal opening in the outer shaft 467, as discussed above. The guidewire 475 may remain inserted into the vasculature, or may be reinserted after removal of the microcatheter 473 and inner shaft 469. Subsequently, as shown in FIG. 15E, at least one additional instrument 573 may be inserted into the vasculature through the outer shaft 467. The guidewire 475 may also be used for positioning the additional instrument 573. The additional instrument 573 may be, for example, a percutaneous transluminal coronary angioplasty balloon or stent, or some other interventional or surgical device. Because the outer shaft 467 remains in position even after removal of the inner shaft 469, the additional instrument 573 may be more easily and safely guided to the target through the outer shaft 467. In this way, there is a reduced risk of trauma to the tissues of the patient when moving the additional instrument 573 through the vasculature, and it is easier to advance to the target location without being diverted.

Although shown and described with respect to one inner shaft and that is centered within the vasculature by the scaffold, embodiments of the present invention can be used with catheters that have multiple inner shafts or microcatheters and no one inner shaft or microcatheter needs to be centered within the vasculature. Alternatively, in a multi-inner shaft configuration, one inner shaft may be centered within the vasculature while one or more other inner shafts are offset from the center of the vasculature. The use of the scaffold CTO to position and cross the lesion, and beneficially position the outer shaft or sheath close to the lesion can be accomplished with the various scaffold embodiments described herein and in the applications incorporated by reference and to which priority is claimed.

The configuration of the devices of the invention may vary. In certain embodiments, the devices are configured for use in vessels that have a diameter from about 2.5 mm to about 4.0 mm. The devices may be configured for an OTW 0.014" guidewire lumen. In certain embodiments, the microcatheter is 3 F microcatheter, which may be up to 150 cm in length. The devices may be configured to be compatible with a 6 FR guide catheter and have a 5 F sheath. Distinguished radiopaque markers may be used on various parts of the device such as the tip of the inner shaft, outer shaft, and/or microcatheter to aid with determining the position of the device in the body. In certain embodiments, the device may have a working length of about 130 cm. A hydrophilic coating may also be used on part of the device. The outer shaft 467 may be formed of a material that maintains a substantially circular cross-section when the inner catheter and scaffold are removed, but the outer shaft may also be soft and flexible enough to be navigable through the tortuous branches of the inner vasculature.

According to embodiments of the present invention, a catheter may be provided that serves a dual purpose. For example, the catheter may be used for a first purpose of advancing a guidewire and inner- or microcatheter to a target area within the vasculature where, in some embodiments, a scaffold is expanded to aid in advancing the guidewire and/or microcatheter through a CTO. Additionally, as a second purpose, the catheter can act as a support catheter that remains in the vasculature such that a distal end of the support catheter remains close to the target location during and/or after the scaffold and microcatheter, for example, are removed from the support catheter. As such, the catheter can serve as a support catheter for additional medical devices or therapeutic agents. These medical devices can include, for example, additional catheters, scopes, imaging or treatment materials/devices, angioplasty balloons, rotoblades, and/or atherectomy devices. However, other medical devices may also be used in conjunction with the guide catheter in its dual purposes. In addition, therapeutic agents such as medicinal, imaging, or irrigation materials may be passed through the support catheter to the target area.

Navigating instruments through the vasculature can be difficult, especially when a target area of the procedure is located within a branch of the vasculature that is off a main trunk of the vasculature. For example, smaller branches are tortuous and extend at angles from the main truck, but instruments will tend to remain straight and thus it can be difficult to steer the instrument into a branch. In addition, the target area may be in still more-distally located branches, which can make reaching the target even more difficult due to the tortuosity of the anatomy. This difficulty is apparent even for devices with a relatively low profile, such as deflated angioplasty balloons, which, though low profile, will tend to proceed straight through a main trunk and resist being steered into side branches.

However, the dual purpose catheter provides a support catheter for reliably reaching the target area after the initial placement of the catheter near the target area. In other words, the support catheter can direct additional medical devices through the tortuous anatomy to the target location, without requiring the difficult re-navigating of the anatomy each time a new device is inserted into the vasculature. Thus, in some embodiments, the dual purpose catheter may be a support catheter that differs in construction from so-called guide catheters in that the support catheter is more flexible to enable navigation of the inner vasculature.

Because the location of a lesion or occlusion, for example, may be in a branch of the vasculature that is one or more than one turn off of the main trunk, the difficulty in reaching the occlusion can vary. Therefore, in embodiments of the present invention, the target area may be in the immediate vicinity of the occlusion, in a branch in which the occlusion is located, or in a branch from which the branch containing the occlusion is disposed (even if the branch containing the occlusion is multiple turns off of the branch of the target area). Even if the specific branch containing the occlusion cannot be reached by the catheter, advancing the distal end of the catheter as close as possible to the occlusion can provide significant benefits over positions that are farther from that "close as possible" location. Thus, in some embodiments of the present invention, it is contemplated that the distal end of the catheter may not be advanced to the immediate vicinity of the occlusion for some patients. Even so, the dual use catheter may provide the same benefit of reaching a target area and for advancing additional medical devices to that target area.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification be considered as exemplary, only, with the true scope and spirit of the invention being indicated by the following claims.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method for positioning a catheter close to an occlusion in a vasculature, the method comprising:
   inserting a catheter apparatus into the vasculature, the catheter apparatus having a microcatheter, an outer shaft and a non-occluding self-expandable scaffold;
   tracking the catheter apparatus along a guidewire located in proximity to the occlusion;
   contacting a leading edge of the occlusion with a distal tip of the outer shaft;
   centering the microcatheter and the non-occluding self-expandable scaffold within the vasculature by expanding the non-occluding self-expandable scaffold within the vasculature;
   advancing the guidewire and the microcatheter out of the distal tip through the occlusion;
   withdrawing the microcatheter and the non-occluding self-expandable scaffold through a proximal opening in the outer shaft, wherein, after withdrawing the microcatheter and non-occluding self-expandable scaffold, the outer shaft remains near the occlusion in the vasculature; and
   advancing an instrument through the proximal opening of the outer shaft and through the occlusion.

2. The method of claim 1, wherein centering the microcatheter and the non-occluding self-expandable scaffold within the vasculature by expanding the non-occluding self-expandable scaffold within the vasculature includes withdrawing or retracting the outer shaft.

3. The method of claim 1, wherein withdrawing the non-occluding self-expandable scaffold through the proximal opening in the outer shaft comprises returning the non-occluding self-expandable scaffold to a non-expanded state.

4. The method of claim 3, wherein returning the non-occluding self-expandable scaffold to the non-expanded state comprises advancing the outer shaft in a distal direction until the non-occluding self-expandable scaffold is contained within the outer shaft.

5. The method of claim 4, the catheter apparatus further comprising an inner shaft, and wherein returning the non-occluding self-expandable scaffold to the non-expanded state comprises moving the inner shaft proximally so that the non-occluding self-expandable scaffold is received within the outer shaft.

6. The method of claim 1, the catheter apparatus further comprising an inner shaft located between the microcatheter and the outer shaft, and further comprising centering the inner shaft with the microcatheter and the non-occluding self-expandable scaffold by expanding the non-occluding self-expandable scaffold.

7. The method of claim 6, further comprising positioning the inner shaft through loops on the non-occluding self-expandable scaffold and positioning the microcatheter through the inner shaft.

8. The method of claim 6, wherein the inner shaft, the outer shaft, the microcatheter and the guidewire are independently moveable.

9. The method of claim 1, wherein the microcatheter supports the guidewire as the guidewire passes through the occlusion.

10. The method of claim 1, wherein the guidewire and the microcatheter are advanced alternatively back and forth to penetrate the occlusion.

11. The method of claim 1, wherein advancing the guidewire through the occlusion comprises penetrating through a portion of the occlusion or through the entirety of the occlusion.

12. The method of claim 1, wherein the microcatheter moves independently of the outer shaft and wherein the microcatheter is withdrawn from the occlusion and the guidewire remains disposed in the occlusion.

13. The method of claim 1, wherein the instrument is one of an angioplasty balloon, a stent, a catheter, a scope, an imaging or treatment device, or medical device.

14. The method of claim 1, wherein the microcatheter and the non-occluding self-expandable scaffold are completely removed from the outer shaft.

15. The method of claim 1, wherein the guidewire assists in guiding the instrument into the occlusion.

* * * * *